(12) United States Patent
Daley et al.

(10) Patent No.: US 8,502,026 B2
(45) Date of Patent: Aug. 6, 2013

(54) TRANSGENIC PLANTS WITH ENHANCED AGRONOMIC TRAITS

(75) Inventors: Maureen Daley, Sacramento, CA (US); Jason Fenner, Sacramento, CA (US); Beth Savidge, Davis, CA (US); Dale Val, Zamora, CA (US); Wei Zheng, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/860,188

(22) Filed: Aug. 20, 2010

(65) Prior Publication Data
US 2011/0047659 A1 Feb. 24, 2011

Related U.S. Application Data

(60) Provisional application No. 61/236,306, filed on Aug. 24, 2009.

(51) Int. Cl.
| | |
|---|---|
| C12N 15/52 | (2006.01) |
| C12N 15/54 | (2006.01) |
| C12N 15/82 | (2006.01) |
| C12N 5/10 | (2006.01) |
| C12N 1/13 | (2006.01) |
| A01H 5/00 | (2006.01) |
| A01H 5/10 | (2006.01) |
| A01H 13/00 | (2006.01) |

(52) U.S. Cl.
USPC ........... 800/281; 435/412; 435/418; 435/419; 435/257.1; 536/23.2; 536/23.74; 800/288; 800/320.1

(58) Field of Classification Search
USPC ....................................................... 800/281
See application file for complete search history.

(56) References Cited

U.S. PATENT DOCUMENTS
7,135,617 B2 * 11/2006 Lardizabal et al. ........... 800/281

OTHER PUBLICATIONS

Gordon-Kamm et al. Transformation of maize cells and regeneration of fertile treansgenic plants (1990) Plant Cell 2: 603-618.*
Weiste et al. Inplanta orfeome analysis by large-scle over-expression of gateway-compatible cDNA clones: screening of ERF transcription factors invoved in abiotic strass defense (2007) Plant J. 52: 382-390.*
Guo et al. Protein tolerance to rendom amino acd change (2004) PNAS 101: 9205-9210.*
Lehner et al. How to use RNA interference (2004) Brief. Functional Genomics, 3: 68-83.*
GenBank Accession No. CBI36129.3, dated Jun. 8, 2010.
GenBank Accession No. AAK19610.1, dated Mar. 15, 2001.
GenBank Accession No. AAM97321.1, dated Aug. 25, 2002.
GenBank Accession No. ADL36724.1, dated Aug. 15, 2010.
GenBank Accession No. ABY41242.1, dated Sep. 17, 2008.
GenBank Accession No. ACJ54445.1, dated Apr. 29, 2010.
GenBank Accession No. BAH85840.1, dated Jul. 22, 2009.
NCBI Reference Sequence No. XP_760084.1, dated Apr. 25, 2006.
NCBI Reference Sequence No. NP_001030857.1, dated Aug. 21, 2009.
NCBI Reference Sequence No. NP_191000.3, dated Aug. 21, 2009.
NCBI Reference Sequence No. XP_002876251.1, dated Jun. 11, 2010.
GenBank Accession No. ADO16346.1, dated Oct. 11, 2010.
GenBank Accession No. ABD16282.1, dated Feb. 13, 2006.
NCBI Reference Sequence No. NP_974430.1, dated Aug. 21, 2009.

* cited by examiner

*Primary Examiner* — David H Kruse
*Assistant Examiner* — Steven Bernacki
(74) *Attorney, Agent, or Firm* — Dentons US LLP; Chunping Li

(57) ABSTRACT

This invention provides transgenic plant cells with recombinant DNA for expression of proteins that are useful for imparting enhanced agronomic trait(s) to transgenic crop plants. This invention also provides transgenic plants and progeny seed comprising the transgenic plant cells where the plants are selected for having an enhanced trait selected from the group of traits consisting of enhanced water use efficiency, enhanced cold tolerance, increased yield, enhanced nitrogen use efficiency, enhanced seed protein, enhanced seed oil and modified oil composition. Also disclosed are methods for manufacturing transgenic seed and plants with enhanced traits.

27 Claims, 3 Drawing Sheets

TRANSGENIC PLANTS WITH ENHANCED AGRONOMIC TRAITS

This application claims the priority of U.S. Provisional Application Ser. No. 61/236,306, filed Aug. 24, 2009, the entire disclosure of which is incorporated herein by reference.

INCORPORATION OF SEQUENCE LISTING

The sequence listing that is contained in the file named "MONS239US_seq.txt", which is 57,344 bytes (measured in MS-WINDOWS), created on Aug. 18, 2010 is filed herewith by electronic submission and incorporated herein by reference.

BACKGROUND OF THE INVENTION

1. Field of the Invention

Disclosed herein are recombinant DNA useful for providing enhanced traits to transgenic plants, seeds, pollen, plant cells and plant nuclei of such transgenic plants, methods of making and using such recombinant DNA, plants, seeds, pollen, plant cells and plant nuclei. Also disclosed are methods of producing hybrid corn seed comprising such recombinant DNA. Also disclosed are plants and seeds having an increased oil content or modified oil composition. All genetic resources disclosed herein were directly obtained from sources that are currently common to the United States; the ancestral sources of each specific genetic material is unknown.

2. Summary of the Invention

This invention provides recombinant DNA encoding or suppressing proteins with at least 95% identity to at least 95% of a sequence selected from SEQ ID NOs: 4-6. The invention further provides isolated polypeptides with at least 95% identity to at least 95% of a sequence selected from SEQ ID NOs: 4-6.

Another aspect of the invention further employs recombinant DNA for expression or suppression of proteins thereby imparting enhanced agronomic traits to the transgenic plants. Recombinant DNA in this invention is provided in a construct comprising a promoter that is functional in plant cells and that is operably linked to DNA that encodes or suppresses a protein having at least 95% identity to at least 95% of a sequence selected from the group consisting of SEQ ID NOs 4-6.

Other aspects of the invention are specifically directed to transgenic plant cells comprising the recombinant DNA of the invention, transgenic plants comprising a plurality of such plant cells, progeny transgenic seed, embryo and transgenic pollen from such plants. Such transgenic plants are selected from a population of transgenic plants regenerated from plant cells transformed with recombinant DNA and expressing or suppressing the protein(s) by screening transgenic plants in the population for an enhanced trait as compared to control plants that do not have said recombinant DNA, where the enhanced trait is selected from group of enhanced traits consisting of enhanced water use efficiency, enhanced cold tolerance, increased yield, enhanced nitrogen use efficiency, enhanced seed protein, enhanced seed oil and modified oil composition. In further embodiments, such transgenic plant cells include polynucleotide stacks which express or suppress multiple proteins of the invention. In a particularly specific embodiment of the invention, such transgenic plants comprise polynucleotide stacks encoding proteins which are at least 95% identical to at least 95% of SEQ ID NOs: 4-6.

In yet another aspect of the invention the plant cells, plants, seeds, embryo and pollen further comprise DNA expressing a protein that provides tolerance from exposure to an herbicide applied at levels that are lethal to a wild type plant cell. Such tolerance is especially useful not only as an advantageous trait in such plants but is also useful in a selection step in the methods of the invention. In aspects of the invention the agent of such herbicide is a glyphosate, dicamba, or glufosinate compound.

Yet other aspects of the invention provide transgenic plants which are homozygous for the recombinant DNA and transgenic seed of the invention from corn, soybean, cotton, canola, alfalfa, wheat or rice plants. In certain embodiments, for instance for practice of various aspects of the invention in Argentina, the recombinant DNA is provided in plant cells derived from corn lines that are and maintain resistance to the Mal de Rio Cuarto virus or the *Puccinia sorghi* fungus or both.

This invention also provides methods for manufacturing non-natural, transgenic seed that can be used to produce a crop of transgenic plants with an enhanced trait resulting from expression of a stably-integrated recombinant DNA construct. More specifically, the method comprises (a) screening a population of plants for an enhanced trait and a recombinant DNA construct, where individual plants in the population can exhibit the trait at a level less than, essentially the same as or greater than the level that the trait is exhibited in control plants, (b) selecting from the population one or more plants that exhibit the trait at a level greater than the level that said trait is exhibited in control plants, (c) collecting seed from a selected plant, (d) verifying that the recombinant DNA is stably integrated in said selected plants, (e) analyzing tissue of a selected plant to determine the production or suppression of a protein having the function of a protein encoded by nucleotides in a sequence of one of SEQ ID NOs: 1-3. In one aspect of the invention, the plants in the population further comprise DNA expressing a protein that provides tolerance to exposure to a herbicide applied at levels that are lethal to wild type plant cells and the selecting is affected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, canola, alfalfa, wheat, rice, sugarcane or sugar beet seed.

Another aspect of the invention provides a method of producing hybrid corn seed comprising acquiring hybrid corn seed from a herbicide tolerant corn plant which also has stably-integrated, recombinant DNA construct comprising a promoter that is (a) functional in plant cells and (b) is operably linked to DNA that encodes or suppresses a protein having the function of a protein encoded by nucleotides in a sequence of one of SEQ ID NOs: 1-3. The methods further comprise producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Another aspect of the invention provides a method of selecting a plant comprising plant cells of the invention by using an immunoreactive antibody to detect the presence or absence of protein expressed or suppressed by recombinant DNA in seed or plant tissue. Yet another aspect of the invention provides anti-counterfeit milled seed having, as an indication of origin, plant cells of this invention.

Still other aspects of this invention relate to transgenic plants with enhanced water use efficiency or enhanced nitrogen use efficiency. For instance, this invention provides methods of growing a corn, cotton, soybean, or canola crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton, soybean or canola crop without added nitrogen fertilizer comprising planting seed having plant cells of the invention which are selected for enhanced nitrogen use efficiency.

Another aspect of the invention provides transgenic plants with enhanced oil levels, including algae. In a particular embodiment, the invention provides transgenic seeds with seed composition improvement including enhanced protein, oil or starch levels.

Some of the recombinant DNA provided by this invention are transcription factors. This invention provides a method of producing a transgenic plant having an enhanced agronomic trait produced by expression of a transcription factor. This method includes identifying target genes of a transcription factor, which includes the steps of assessing a dataset of expression profiles of a transcription factor gene and other genes and analyzing said dataset to determine a subset of genes that are regulated by said transcription factor, and cloning the coding sequence of at least one of the subset of genes into a plant transformation vector and transforming a plant with such vector.

Furthermore, this invention provides novel genes of *Glycine max* GLABRA2 (Gm.GL2) and *Rhodosporidium toruloides* DGAT2 (Rt.DGAT2); and an *Arabidopsis/Brassica* chimeric DNA construct (At.Bn.Otf1) of an oil transcription factor, coding for proteins as set forth in SEQ ID NO:4 through SEQ ID NO:6, respectively, which are particularly useful for generating transgenic crop plants having seeds with enhanced oil levels.

DETAILED DESCRIPTION OF THE INVENTION

Figure 1:
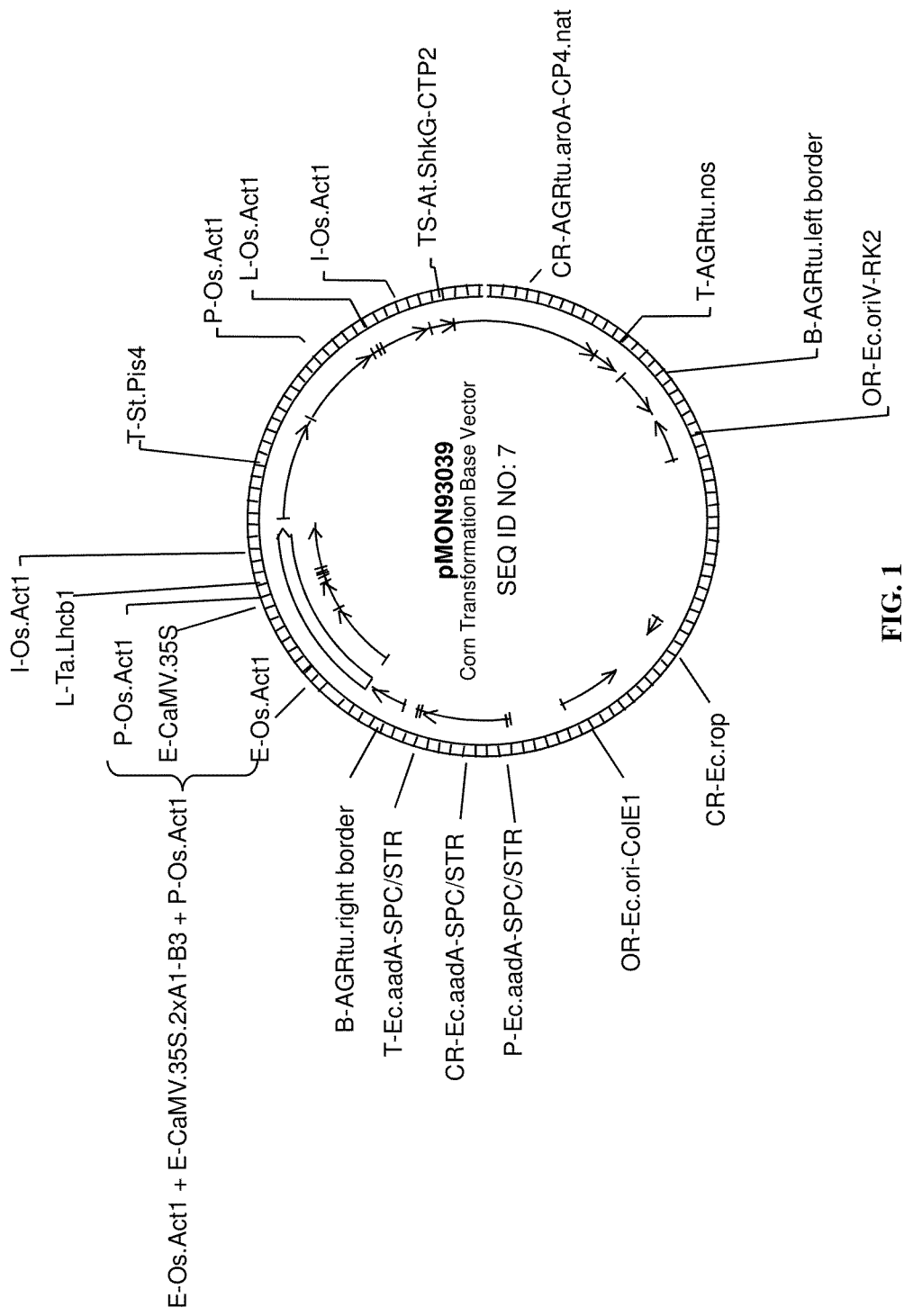
FIGS. 1-3 are plasmid maps of base vectors for corn, soybean and cotton transformation.

In the attached sequence listing:

SEQ ID NO:1-3 are nucleotide sequences of the coding strand of DNA for "genes" used in the recombinant DNA imparting an enhanced trait in plant cells, i.e. each represents a coding sequence for a protein;

SEQ ID NO:4-6 are amino acid sequences of the cognate protein of the "genes" with nucleotide coding sequences 1-3;

SEQ ID NO:7 is a nucleotide sequence of a base plasmid vector useful for corn transformation;

SEQ ID NO:8 is a nucleotide sequence of a base plasmid vector useful for soybean and canola transformation;

SEQ ID NO:9 is a nucleotide sequence of a base plasmid vector useful for cotton transformation;

As used herein a "plant cell" means a plant cell that is transformed with stably-integrated, non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" includes a plant, plant part, plant cells or seed whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. With reference to homologous genes, homologs include orthologs, i.e. genes expressed in different species that evolved from a common ancestral genes by speciation and encode proteins retain the same function, but do not include paralogs, i.e. genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins have at least 60% identity, more preferably about 65% or higher, more preferably about 70% or higher, more preferably at least 75%, more preferably at least 80%, more preferably at least 85%, more preferably at least 90% identity, more preferably at least 95, 96, 97, 98, or 99% identity over the full length of a protein identified as being associated with imparting an enhanced trait when expressed in plant cells. In one aspect of the invention homolog proteins have an amino acid sequence that has at least 90% identity to a consensus amino acid sequence of proteins and homologs disclosed herein.

Homologs are identified by comparison of amino acid sequence, e.g. manually or by use of a computer-based tool using known homology-based search algorithms such as the suite of BLAST programs available from NCBI. A local sequence alignment program, e.g. BLAST, can be used to search a database of sequences to find similar sequences, and the summary Expectation value (E-value) used to measure the sequence base similarity. Because a protein hit with the best E-value for a particular organism may not necessarily be an ortholog, i.e. have the same function, or be the only ortholog, a reciprocal query is used to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best hit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

Percent identity describes the extent to which the sequences of DNA or protein segments are invariant in an alignment of sequences, for example nucleotide sequences or amino acid sequences. An alignment of sequences is created by manually aligning two sequences, e.g. a stated sequence, as provided herein, as a reference, and another sequence, to produce the highest number of matching elements, e.g. individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred." Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a recombinant DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein "suppressed" means decreased, e.g. a protein is suppressed in a plant cell when there is a decrease in the amount and/or activity of the protein in the plant cell. The presence or activity of the protein can be decreased by any amount up to and including a total loss of protein expression and/or activity.

As used herein a "control plant" means a plant that does not contain the recombinant DNA that imparts an enhanced trait. A control plant is used to identify and select a transgenic plant that has an enhanced trait. A suitable control plant can be a non-transgenic plant of the parental line used to generate a transgenic plant, i.e. devoid of recombinant DNA. A suitable control plant may in some cases be a progeny of a hemizygous transgenic plant line that does not contain the recombinant DNA, known as a negative segregant.

As used herein an "enhanced trait" means a characteristic of a transgenic plant that includes, but is not limited to, an enhanced agronomic trait characterized by enhanced plant morphology, physiology, growth and development, yield, nutritional enhancement, disease or pest resistance, or environmental or chemical tolerance. In more specific aspects of this invention an enhanced trait is selected from a group of enhanced traits consisting of enhanced water use efficiency, enhanced cold tolerance, increased yield, enhanced nitrogen use efficiency, enhanced seed protein, enhanced oil production in the seed or other tissue and modified oil composition. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil; seed molecules such as protein and starch; and oil components as may be manifest by alterations in the ratios of seed components.

Recombinant DNA constructs are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Useful promoters derived from plant genes are found in U.S. Pat. No. 5,641,876 which discloses a rice actin promoter, U.S. Pat. No. 7,151,204 which discloses a maize chloroplast aldolase promoter and a maize aldolase (FDA) promoter, and US Patent Application Publication 2003/0131377 A1 which discloses a maize nicotianamine synthase promoter. These and numerous other promoters that function in plant cells are known to those skilled in the art and available for use in recombinant polynucleotides of the present invention to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene. See also US Patent Application Publication 2002/0192813A1 which discloses 5', 3' and intron elements useful in the design of effective plant expression vectors.

In other aspects of the invention, sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252), zein Z27 as disclosed by Russell et al. (1997) *Transgenic Res.* 6(2):157-166), globulin 1 as disclosed by Belanger et al (1991) *Genetics* 129:863-872), glutelin 1 as disclosed by Russell (1997) supra), and peroxiredoxin antioxidant (Peri) as disclosed by Stacy et al. (1996) *Plant Mol Biol.* 31(6):1205-1216.

Recombinant DNA constructs useful in this invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aestivum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/0192813 A1; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. 5,188,642 and U.S. Pat. No. 5,728,925. For description of the transit peptide region of an *Arabidopsis* EPSPS gene useful in the present invention, see Klee, H. J. et al (MGG (1987) 210:437-442).

Recombinant DNA constructs for gene suppression can be designed for any of a number the well-known methods for suppressing transcription of a gene, the accumulation of the mRNA corresponding to that gene or preventing translation of the transcript into protein. Posttranscriptional gene suppression can be practically effected by transcription of RNA that forms double-stranded RNA (dsRNA) having homology to mRNA produced from a gene targeted for suppression.

Gene suppression can also be achieved by insertion mutations created by transposable elements which may also prevent gene function. For example, in many dicot plants, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest.

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringensis* to provide resistance against lepidopteran, coleopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al., (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (*Nucl. Acids Res.* 18:2188-2193 (1990)) for imparting tolerance to sulfonylurea herbicides; polynucleotide molecules known as bar genes disclosed in DeBlock, et al. (*EMBO J.* 6:2513-2519, 1987) for imparting glufosinate and bialaphos tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 5,986,175 and US Patent Application Publication 2003/0150017 A1. Methods and tools for utilization of the current gene sequences for enhanced oil production in algae can be found in U.S. Pat. No. 6,027,900.

Plant Cell Transformation Methods

Numerous methods for transforming chromosomes in a plant cell nucleus with recombinant DNA are known in the art and are used in methods of preparing a transgenic plant cell nucleus cell, and plant. Two effective methods for such transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice); *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), US Patent Application Publication 2004/0087030 A1 (cotton), and US Patent Application Publication 2001/0042257 A1 (sugar beet); and algal transformation can be demonstrated in Kumar et al., *Genetic Transformation of the Green Alga — Chlamydomonas reinhardtii by Agrobacterium tumefaciens*, PLANT SCI. 166(3) pp 731-38 (2004), all of which are incorporated herein by reference for enabling the production of transgenic plants. Transformation of plant material is practiced in tissue culture on a nutrient media, i.e. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from transgenic plant cells having a transgenic nucleus of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or another trait that provides increased plant value, including, for example, improved seed quality. Of particular interest are plants having enhanced water use efficiency, enhanced cold tolerance, increased yield, enhanced nitrogen use efficiency, enhanced seed protein, enhanced seed oil and modified oil composition.

Table 1 provides a list of protein encoding DNA ("genes") that are useful as recombinant DNA for production of transgenic plants with enhanced agronomic traits; the elements of Table 1 are described by reference to:

"PEP SEQ ID NO" identifies an amino acid sequence from SEQ ID NO:4 to 6.

"NUC SEQ ID NO" identifies a DNA sequence from SEQ ID NO:1 to 3.

"Gene ID" refers to an arbitrary identifier.

"Gene Name" denotes a common name for the protein encoded by the recombinant DNA preceded by the abbreviated genus and species as fully defined in the sequence listing. The + or − preceding the gene name indicates whether the protein is expressed (+) or suppressed (−) in plants to provide an enhanced trait.

"Annotation" refers to a description of the top hit protein obtained from an amino acid sequence query of each PEP SEQ ID NO to GENBANK database of the National Center for Biotechnology Information (ncbi).

TABLE 1

List of certain genes useful as recombinant DNA for production of transgenic plants with enhanced agronomic traits.

| NUC SEQ ID NO | PEP SEQ ID NO | Gene ID | Gene Name | Annotation |
|---|---|---|---|---|
| 1 | 4 | GLABRA2 | +Gm. GL2 | BNLGHi8377 [*Gossypium hirsutum*] |
| 2 | 5 | Diacylglycerol acyltransferase-2a | +Rt. DGAT2 | Diacylglycerol acyltransferase [*Rhodosporidium toruloides*] |
| 3 | 6 | Oil transcription factor-1 | +At. Bn. Otf1 chimera | activator of sporamin LUC 1 [*Arabidopsis thaliana*] WRINKLED 1 [*Arabidopsis thaliana*] |

Selection Methods for Transgenic Plants with Enhanced Agronomic Traits

Within a population of transgenic plants each regenerated from a plant cell having a nucleus with recombinant DNA many plants that survive to fertile transgenic plants that produce seeds and progeny plants will not exhibit an enhanced agronomic trait. Selection from the population is necessary to identify one or more transgenic plant cells having a transgenic nucleus that can provide plants with the enhanced trait. Transgenic plants having enhanced traits are selected from populations of plants regenerated or derived from plant cells transformed as described herein by evaluating the plants in a variety of assays to detect an enhanced trait, e.g. enhanced water use efficiency, enhanced cold tolerance, increased yield, enhanced nitrogen use efficiency, enhanced seed protein, enhanced seed oil and modified oil composition. These assays also may take many forms including, but not limited to, direct screening for the trait in a greenhouse or field trial or by screening for a surrogate trait. Such analyses can be directed to detecting changes in the chemical composition, biomass, physiological properties, or morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weights; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, phenotypic characteristics of harvested grain may be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates useful screening assays for corn traits using hybrid corn plants. The assays can be readily adapted for screening other plants such as canola, cotton and soybean either as hybrids or inbreds.

Transgenic corn plants having nitrogen use efficiency are identified by screening in fields with three levels of nitrogen (N) fertilizer being applied, e.g. low level (0 N), medium level (80 lb/ac) and high level (180 lb/ac). Plants with enhanced nitrogen use efficiency provide higher yield as compared to control plants.

Transgenic corn plants having enhanced yield are identified by screening using progeny of the transgenic plants over multiple locations with plants grown under optimal production management practices and maximum weed and pest control. A useful target for improved yield is a 5% to 10% increase in yield as compared to yield produced by plants grown from seed for a control plant. Selection methods may be applied in multiple and diverse geographic locations, for example up to 16 or more locations, over one or more planting seasons, for example at least two planting seasons, to statistically distinguish yield improvement from natural environmental effects.

Transgenic corn plants having enhanced water use efficiency are identified by screening plants in an assay where water is withheld for a period to induce stress followed by watering to revive the plants. For example, a useful selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Transgenic corn plants having enhanced cold tolerance are identified by screening plants in a cold germination assay and/or a cold tolerance field trial. In a cold germination assay trays of transgenic and control seeds are placed in a growth chamber at 9.7° C. for 24 days (no light). Seeds having higher germination rates as compared to the control are identified as having enhanced cold tolerance. In a cold tolerance field trial plants with enhanced cold tolerance are identified from field planting at an earlier date than conventional Spring planting for the field location. For example, seeds are planted into the ground around two weeks before local farmers begin to plant corn so that a significant cold stress is exerted onto the crop, named as cold treatment. Seeds also are planted under local optimal planting conditions such that the crop has little or no exposure to cold condition, named as normal treatment. At each location, seeds are planted under both cold and normal conditions preferably with multiple repetitions per treatment.

Transgenic corn plants having seeds with increased protein and/or oil levels are identified by analyzing progeny seed for protein and/or oil. Near-infrared transmittance spectrometry is a non-destructive, high-throughput method that is useful to determine the composition of a bulk seed sample for properties listed in Table 2.

TABLE 2

Composition of bulk seed samples.

| Typical sample(s): | Whole grain corn and soybean seeds |
|---|---|
| Typical analytical range: | Corn-moisture 5-15%, oil 5-20%, protein 5-30%, starch 50-75%, and density 1.0-1.3%. Soybean-moisture 5-15%, oil 15-25%, and protein 35-50%. |

Although the plant cells and methods of this invention can be applied to any plant cell, plant, seed or pollen, e.g. any fruit, vegetable, grass, tree or ornamental plant, the various aspects of the invention are preferably applied to corn, soybean, cotton, canola, alfalfa, wheat, rice, sugarcane, and sugar beet plants. In many cases the invention is applied to corn plants that are inherently resistant to disease from the Mal de Rio Cuarto virus or the *Puccina sorghi* fungus or both.

EXAMPLES

The following examples are included to demonstrate aspects of the invention, those of skill in the art should, in light of the present disclosure, appreciate that many changes can be made in the specific aspects which are disclosed and still obtain a like or similar results without departing from the spirit and scope of the invention.

Example 1

Plant Expression Constructs

This example illustrates the construction of plasmids for transferring recombinant DNA into a plant cell nucleus that can be regenerated into transgenic plants.

A. Plant Expression Constructs for Corn Transformation

A base corn transformation vector pMON93039, as set forth in SEQ ID NO:7, illustrated in Table 3 and FIG. 1, is fabricated for use in preparing recombinant DNA for *Agrobacterium*-mediated transformation into corn tissue.

TABLE 3

Components of exemplary plant transformation vector.

| Function | Name | Annotation | Coordinates of SEQ ID NO: 7 |
|---|---|---|---|
| *Agrobacterium* T-DNA transfer | B-AGRtu. right border | Agro right border sequence, essential for transfer of T-DNA. | 11364-11720 |
| Gene of interest expression cassette | E-Os.Act1 | Upstream promoter region of the rice actin 1 gene | 19-775 |
| | E-CaMV.35S. 2xAl-B3 | Duplicated35S A1-B3 domain without TATA box | 788-1120 |
| | P-Os.Act1 | Promoter region of the rice actin 1 gene | 1125-1204 |
| | L-Ta.Lhcb1 | 5' untranslated leader of wheat major chlorophyll a/b binding protein | 1210-1270 |
| | I-Os.Act1 | First intron and flanking UTR exon sequences from the rice actin 1 gene | 1287-1766 |
| | T-St.Pis4 | 3' non-translated region of the potato proteinase inhibitor II gene which functions to direct polyadenylation of the mRNA | 1838-2780 |
| Plant selectable marker expression cassette | P-Os.Act1 | Promoter from the rice actin 1 gene | 2830-3670 |
| | L-Os.Act1 | First exon of the rice actin 1 gene | 3671-3750 |
| | I-Os.Act1 | First intron and flanking UTR exon sequences from the rice actin 1 gene | 3751-4228 |
| | TS-At.ShkG-CTP2 | Transit peptide region of *Arabidopsis* EPSPS | 4238-4465 |
| | CR-AGRtu.aroA-CP4.nat | Coding region for bacterial strain CP4 native aroA gene. | 4466-5833 |

TABLE 3-continued

Components of exemplary plant transformation vector.

| Function | Name | Annotation | Coordinates of SEQ ID NO: 7 |
|---|---|---|---|
| | T-AGRtu.nos | A 3' non-translated region of the nopaline synthase gene of *Agrobacterium tumefaciens* Ti plasmid which functions to direct polyadenylation of the mRNA. | 5849-6101 |
| *Agrobacterium* T-DNA transfer | B-AGRtu.left border | Agro left border sequence, essential for transfer of T-DNA. | 6168-6609 |
| Maintenance in *E. coli* | OR-Ec.oriV-RK2 | The vegetative origin of replication from plasmid RK2. | 6696-7092 |
| | CR-Ec.rop | Coding region for repressor of primer from the ColE1 plasmid. Expression of this gene product interferes with primer binding at the origin of replication, keeping plasmid copy number low. | 8601-8792 |
| | OR-Ec.ori-ColE1 | The minimal origin of replication from the *E. coli* plasmid ColE1. | 9220-9808 |
| | P-Ec.aadA-SPC/STR | Promoter for Tn7 adenylyltransferase (AAD(3")) | 10339-10380 |
| | CR-Ec.aadA-SPC/STR | Coding region for Tn7 adenylyltransferase (AAD(3")) conferring spectinomycin and streptomycin resistance. | 10381-11169 |
| | T-Ec.aadA-SPC/STR | 3' UTR from the Tn7 adenylyltransferase (AAD(3")) gene of *E. coli*. | 11170-11227 |

To construct transformation vectors for expressing a protein identified in Table 1, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the intron element (coordinates 1287-1766) and the polyadenylation element (coordinates 1838-2780).

To construct transformation vectors for suppressing a protein identified in Table 1, the amplified protein coding nucleotides are assembled in a sense and antisense arrangement and inserted into the base vector at the insertion site in the gene of interest expression cassette to provide transcribed RNA that will form a double-stranded RNA for RNA interference suppression of the protein.

B. Plant Expression Constructs for Soy and Canola Transformation

Figure 2:
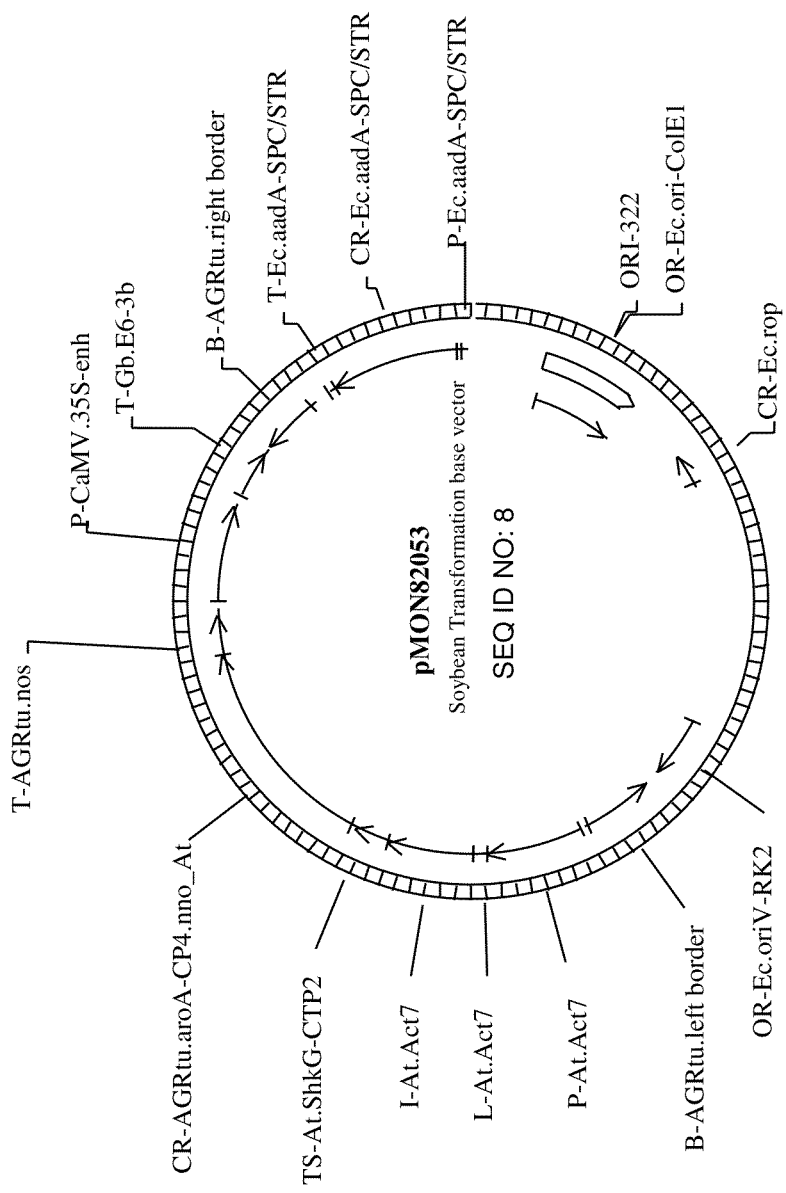

Vectors for use in transformation of soybean and canola tissue are prepared having the elements of expression vector pMON82053 (SEQ ID NO:8) as shown in Table 4 below and FIG. 2.

TABLE 4

Genetic components of exemplary plant expression vector.

| Function | Name | Annotation | Coordinates of SEQ ID NO: 8 |
|---|---|---|---|
| *Agrobacterium* T-DNA transfer | B-AGRtu.left border | Agro left border sequence, essential for transfer of T-DNA. | 6144-6585 |
| Plant selectable marker expression cassette | P-At.Act7 | Promoter from the *Arabidopsis* actin 7 gene | 6624-7861 |
| | L-At.Act7 | 5'UTR of *Arabidopsis* Act7 gene | |
| | I-At.Act7 | Intron from the *Arabidopsis* actin7 gene | |
| | TS-At.ShkG-CTP2 | Transit peptide region of *Arabidopsis* EPSPS | 7864-8091 |
| | CR-AGRtu.aroA-CP4.nno_At | Synthetic CP4 coding region with dicot preferred codon usage. | 8092-9459 |
| | T-AGRtu.nos | A 3' non-translated region of the nopaline synthase gene of *Agrobacterium tumefaciens* Ti plasmid which functions to direct polyadenylation of the mRNA. | 9466-9718 |

TABLE 4-continued

Genetic components of exemplary plant expression vector.

| Function | Name | Annotation | Coordinates of SEQ ID NO: 8 |
|---|---|---|---|
| Gene of interest expression cassette | P-CaMV.35S-enh | Promoter for 35S RNA from CaMV containing a duplication of the −90 to −350 region. | 1-613 |
| | T-Gb.E6-3b | 3' untranslated region from the fiber protein E6 gene of sea-island cotton. | 688-1002 |
| *Agrobacterium* T-DNA transfer | B-AGRtu.right border | Agro right border sequence, essential for transfer of T-DNA. | 1033-1389 |
| Maintenance in *E. coli* | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the origin of replication, keeping plasmid copy number low. | 3961-4152 |
| | OR-Ec.ori-ColE1 | The minimal origin of replication from the *E. coli* plasmid ColE1. | 2945-3533 |
| | P-Ec.aadA-SPC/STR | Promoter for Tn7 adenylyltransferase (AAD(3")) | 2373-2414 |
| | CR-Ec.aadA-SPC/STR | Coding region for Tn7 adenylyltransferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of *E. coli*. | 1526-1583 |

To construct transformation vectors for expressing a protein identified in Table 1, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the promoter element (coordinates 1-613) and the polyadenylation element (coordinates 688-1002).

To construct transformation vectors for suppressing a protein identified in Table 1, the amplified protein coding nucleotides are assembled in a sense and antisense arrangement and inserted into the base vector at the insertion site in the gene of interest expression cassette to provide transcribed RNA that will form a double-stranded RNA for RNA interference suppression of the protein.

C. Cotton Transformation Vector

Figure 3:
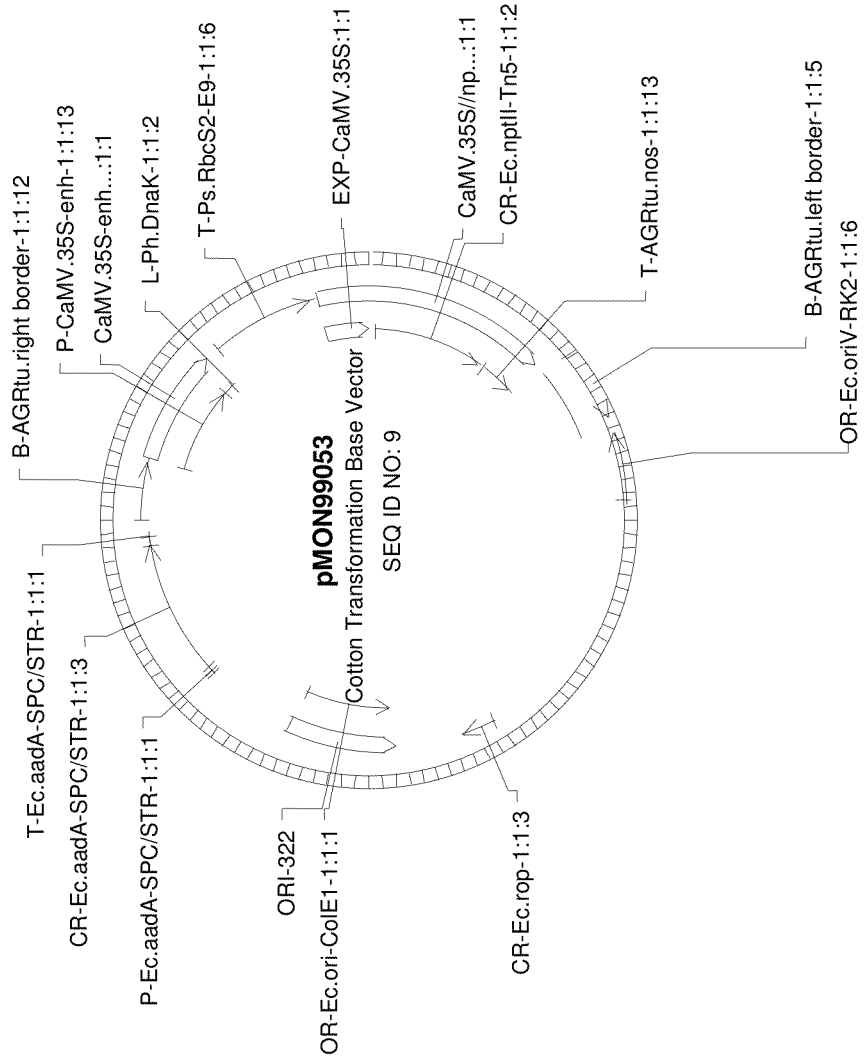

Plasmids for use in transformation of cotton tissue are prepared with elements of expression vector pMON99053 (SEQ ID NO:9) as shown in Table 5 below and FIG. 3.

TABLE 5

Genetic components of exemplary plant expression vector.

| Function | Name | Annotation | Coordinates of SEQ ID NO: 9 |
|---|---|---|---|
| *Agrobacterium* T-DNA transfer | B-AGRtu.right border | Agro right border sequence, essential for transfer of T-DNA. | 1-357 |
| Gene of interest expression cassette | Exp-CaMV.35S-enh + Ph.DnaK | Enhanced version of the 35S RNA promoter from CaMV plus the *petunia* hsp70 5' untranslated region | 388-1091 |
| | T-Ps.RbcS2-E9 | The 3' non-translated region of the pea RbcS2 gene which functions to direct polyadenylation of the mRNA. | 1165-1797 |
| Plant selectable marker expression cassette | Exp-CaMV.35S | Promoter and 5' untranslated region from the 35S RNA of CaMV | 1828-2151 |
| | CR-Ec.nptII-Tn5 | Coding region for neomycin phosphotransferase gene from transposon Tn5 which confers resistance to neomycin and kanamycin. | 2185-2979 |

TABLE 5-continued

Genetic components of exemplary plant expression vector.

| Function | Name | Annotation | Coordinates of SEQ ID NO: 9 |
|---|---|---|---|
| | T-AGRtu.nos | A 3' non-translated region of the nopaline synthase gene of *Agrobacterium tumefaciens* Ti plasmid which functions to direct polyadenylation of the mRNA. | 3011-3263 |
| *Agrobacterium* T-DNA transfer | B-AGRtu.left border | Agro left border sequence, essential for transfer of T-DNA. | 3309-3750 |
| Maintenance in *E. coli* | OR-Ec.oriV-RK2 | The vegetative origin of replication from plasmid RK2. | 3837-4233 |
| | CR-Ec.rop | Coding region for repressor of primer from the ColE1 plasmid. Expression of this gene product interferes with primer binding at the origin of replication, keeping plasmid copy number low. | 5742-5933 |
| | OR-Ec.ori-ColE1 | The minimal origin of replication from the *E. coli* plasmid ColE1. | 6361-6949 |
| | P-Ec.aadA-SPC/STR | Promoter for Tn7 adenylyltransferase (AAD(3")) | 7480-7521 |
| | CR-Ec.aadA-SPC/STR | Coding region for Tn7 adenylyltransferase (AAD(3")) conferring spectinomycin and streptomycin resistance. | 7522-8310 |
| | T-Ec.aadA-SPC/STR | 3' UTR from the Tn7 adenylyltransferase (AAD(3")) gene of *E. coli*. | 8311-8368 |

To construct transformation vectors for expressing a protein identified in Table 1, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the promoter element (coordinates 388-1091) and the polyadenylation element (coordinates 1165-1797).

To construct transformation vectors for suppressing a protein identified in Table 1, the amplified protein coding nucleotides are assembled in a sense and antisense arrangement and inserted into the base vector at the insertion site in the gene of interest expression cassette to provide transcribed RNA that will form a double-stranded RNA for RNA interference suppression of the protein.

Example 2

Corn Transformation

This example illustrates transformation methods useful in producing a transgenic nucleus in a corn plant cell, and the plants, seeds and pollen produced from a transgenic cell with such a nucleus having an enhanced trait, i.e. enhanced water use efficiency, enhanced cold tolerance, increased yield, enhanced nitrogen use efficiency, enhanced seed protein, enhanced seed oil and modified oil composition. A plasmid vector is prepared by cloning DNA from SEQ ID NO:1, SEQ ID NO:2 or SEQ ID NO:3 into the gene of interest expression cassette in the base vector for use in corn transformation of corn tissue provided in Example 1, Table 3.

For *Agrobacterium*-mediated transformation of corn embryo cells corn plants of a readily transformable line are grown in the greenhouse and ears are harvested when the embryos are 1.5 to 2.0 mm in length. Ears are surface sterilized by spraying or soaking the ears in 80% ethanol, followed by air drying. Immature embryos are isolated from individual kernels on surface-sterilized ears. Prior to inoculation of maize cells, *Agrobacterium* cells are grown overnight at room temperature. Immature maize embryo cells are inoculated with *Agrobacterium* shortly after excision, and incubated at room temperature with *Agrobacterium* for 5-20 minutes. Immature embryo plant cells are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformed plant cells are recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

The above process is repeated to produce multiple events of transgenic corn plant cells that are transformed with recombinant DNA from each of the genes identified in Table 1. Events are designed to produce in the transgenic cells one of the proteins identified in Table 1. Progeny transgenic plants and seed of the transformed plant cells are screened for enhanced water use efficiency, enhanced cold tolerance, increased yield, enhanced nitrogen use efficiency, enhanced seed protein, enhanced seed oil and modified oil composition. From each group of multiple events of transgenic plants with a specific recombinant DNA from Table 1 the event that produces the greatest enhancement in yield, water use efficiency, nitrogen use efficiency, enhanced cold tolerance, enhanced seed protein, enhanced seed oil and modified oil composition is identified and progeny seed is selected for commercial development.

Example 3

Soybean Transformation

This example illustrates plant transformation useful in producing a transgenic nucleus in a soybean plant cell, and the plants, seeds and pollen produced from a transgenic cell with such a nucleus having an enhanced trait, i.e. enhanced water use efficiency, enhanced cold tolerance, increased yield, enhanced nitrogen use efficiency, enhanced seed protein, enhanced seed oil and modified oil composition.

For *Agrobacterium* mediated transformation, soybean seeds are imbibed overnight and the meristem explants excised. The explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed imbibition, and wounded using sonication. Following wounding, explants are placed in co-culture for 2-5 days at which point they are transferred to selection media for 6-8 weeks to allow selection and growth of transgenic shoots. Resistant shoots are harvested at approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil.

The above process is repeated to produce multiple events of transgenic soybean plant cells that are transformed with recombinant DNA from each of the genes identified in Table 1. Events are designed to produce in the transgenic cells one of the proteins identified in Table 1. Progeny transgenic plants and seed of the transformed plant cells are screened for enhanced water use efficiency, enhanced cold tolerance, increased yield, enhanced seed protein, enhanced seed oil and modified oil composition. From each group of multiple events of transgenic plants with a specific recombinant DNA from Table 1 the event that produces the greatest enhancement in yield, water use efficiency, nitrogen use efficiency, enhanced cold tolerance, enhanced seed protein, enhanced seed oil and modified oil composition is identified and progeny seed is selected for commercial development.

Example 4

Cotton Transgenic Plants with Enhanced Agronomic Traits

This example illustrates plant transformation useful in producing a transgenic nucleus in a cotton plant cell, and the plants, seeds and pollen produced from a transgenic cell with such a nucleus having an enhanced trait, i.e. enhanced water use efficiency, increased yield, enhanced nitrogen use efficiency, enhanced seed oil and modified oil composition.

Transgenic cotton plants containing each recombinant DNA having a sequence from SEQ ID NO:1 through SEQ ID NO:3 are obtained by transforming with recombinant DNA from each of the genes identified in Table 1 using *Agrobacterium*-mediated tranformation. The above process is repeated to produce multiple events of transgenic cotton plant cells that are transformed with recombinant DNA from each of the genes identified in Table 1. Events are designed to produce in the transgenic cells one of the proteins identified in Table 1.

From each group of multiple events of transgenic plants with a specific recombinant DNA from Table 1 the event that produces the greatest enhancement in yield, water use efficiency, nitrogen use efficiency, enhanced cold tolerance, enhanced seed protein, enhanced seed oil and modified oil composition is identified and progeny seed is selected for commercial development.

Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, i.e. cotton variety ST474, cotton variety FM 958, and cotton variety Siokra L-23, are used to compare the relative performance of the transgenic cotton plants containing the recombinant DNA.

Transgenic cotton plants with enhanced yield and water use efficiency are identified by growing under variable water conditions. Specific conditions for cotton include growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, i.e. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates, and improved fiber parameters.

Example 5

Canola Transformation

This example illustrates plant transformation useful in producing the transgenic canola plants of this invention and the production and identification of transgenic seed for transgenic canola having enhanced water use efficiency, enhanced cold tolerance, increased yield, enhanced nitrogen use efficiency, enhanced seed protein, enhanced seed oil and modified oil composition.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection media to promote growth of transgenic shoots, followed by growth of roots from the transgenic shoots. The selected plantlets are then transferred to the greenhouse and potted in soil. Molecular characterizations are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant.

Transgenic canola plant cells are transformed with each of the recombinant DNA identified in Table 1. The above process is repeated to produce multiple events of transgenic canola plant cells that are transformed with recombinant DNA from each of the genes identified in Table 1. Events are designed to produce in the transgenic cells one of the proteins identified in Table 1. Progeny transgenic plants and seed of the transformed plant cells are screened for enhanced water use efficiency, enhanced cold tolerance, increased yield, enhanced seed protein, enhanced seed oil and modified oil composition. From each group of multiple events of transgenic plants with a specific recombinant DNA from Table 1 the event that produces the greatest enhancement in yield, water use efficiency, nitrogen use efficiency, enhanced cold tolerance, enhanced seed protein, enhanced seed oil and modified oil composition is identified and progeny seed is selected for commercial development.

Similarly such transformation can be done for various algae, with progeny selected for heightened oil production levels.

Example 6

Homolog Identification

This example illustrates the identification of homologs of proteins encoded by the DNA identified in Table 1 which is used to provide transgenic seed and plants having enhanced agronomic traits. From the sequence of the homologs, homologous DNA sequence can be identified for preparing additional transgenic seeds and plants of this invention with enhanced agronomic traits.

An "All Protein Database" is constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" is constructed of known protein sequences of the organism; it is a subset of the All Protein Database based on the NCBI taxonomy ID for the organism.

The All Protein Database is queried using amino acid sequences provided herein as SEQ ID NO:4 through SEQ ID NO:6 using NCBI "blastp" program with E-value cutoff of 1e-8. Up to 1000 top hits are kept, and separated by organism names. For each organism other than that of the query sequence, a list is kept for hits from the query organism itself with a more significant E-value than the best hit of the organism. The list contains likely duplicated genes of the polynucleotides provided herein, and is referred to as the Core List. Another list is kept for all the hits from each organism, sorted by E-value, and referred to as the Hit List.

The Organism Protein Database is queried using polypeptide sequences provided herein as SEQ ID NO:4 through SEQ ID NO:6 using NCBI "blastp" program with E-value cutoff of 1e-4. Up to 1000 top hits are kept. A BLAST searchable database is constructed based on these hits, and is referred to as "SubDB". SubDB is queried with each sequence in the Hit List using NCBI "blastp" program with E-value cutoff of 1e-8. The hit with the best E-value is compared with the Core List from the corresponding organism. The hit is deemed a likely ortholog if it belongs to the Core List, otherwise it is deemed not a likely ortholog and there is no further search of sequences in the Hit List for the same organism. Homologs from a large number of distinct organisms can be identified and reported.

Recombinant DNA constructs are prepared using the DNA encoding each of the identified homologs and the constructs are used to prepare multiple events of transgenic corn, soybean, canola and cotton plants as illustrated in Examples 2-5. Plants are regenerated from the transformed plant cells and used to produce progeny plants and seed that are screened for enhanced water use efficiency, enhanced cold tolerance, increased yield, enhanced nitrogen use efficiency, enhanced seed protein, enhanced seed oil and modified oil composition. From each group of multiple events of transgenic plants with a specific recombinant DNA for a homolog the event that produces the greatest enhancement in yield, water use efficiency, nitrogen use efficiency, enhanced cold tolerance, enhanced seed protein, enhanced seed oil and modified oil composition is identified and progeny seed is selected for commercial development.

What is claimed is:

1. A recombinant DNA molecule comprising a promoter that is functional in a plant cell and that is operably linked to a polynucleotide that,
encodes a protein:
   i) having the ammo acid sequence of SEQ ID NO:5; or
   ii) having an amino acid sequence having at least 95% identity to SEQ ID NO:5 over its full length, wherein the sequence exhibits diacylglycerol acyltransferase activity.

2. The recombinant DNA molecule of claim 1 wherein said molecule further comprises at least one regulatory element selected from the group consisting of a 5' untranslated region, intron, ' untranslated region, and a transit peptide region.

3. A transgenic plant cell comprising a recombinant DNA molecule comprising a promoter that functional in a plant cell and that is operably linked to as polynucleotide that
encodes a protein:
   i) having the amino acid sequence of SEQ ID NO:5; or
   ii) having an amino acid sequence having at least 95% identity to SEQ ID NO:5 over its full length, wherein the sequence exhibits diacylglycerol acyltransferase activity.

4. The transgenic plant cell of claim 3 wherein said recombinant DNA molecule is stably integrated into a chromosome in a plant cell nucleus.

5. The transgenic plant cell of claim 3 wherein said plant cell is selected by screening a population of transgenic plant cells that have been transformed with said molecule for an enhanced trait as compared to control plant cells; and wherein said enhanced trait is [enhanced water use efficiency, enhanced cold tolerance,] increased yield, [enhanced nitrogen use efficiency, enhanced seed protein,] enhanced seed oil, or modified oil composition.

6. The transgenic plant cell of claim 3 further comprising a DNA molecule expressing a protein that provides tolerance from exposure to a herbicide that is lethal to a wild type of said plant cell.

7. The transgenic plant cell of claim 6 wherein said herbicide comprises a glyphosate, dicamba, or glufosinate compound.

8. The transgenic plant cell of claim 3 wherein said plant cell is part of a transgenic plant.

9. The transgenic plant cell of claim 3 wherein said plant cell is in a plant seed.

10. The transgenic plant cell of claim 9 wherein said seed is from a corn, soybean, cotton, canola, alfalfa, wheat, rice, sugarcane, or sugar beet plant.

11. The transgenic plant cell of claim 3 further comprising at least one DNA molecule expressing a protein that provides an enhanced trait as compared to control plant cells; and wherein the enhanced trait is [enhanced water use efficiency, enhanced cold tolerance,] increased yield, [enhanced nitrogen use efficiency, enhanced seed protein,] enhanced seed oil, or modified oil composition.

12. The transgenic plant cell of claim 6 further comprising at least one DNA molecule expressing a protein that provides an enhanced trait as compared to control plant cells; and wherein the enhanced trait is [enhanced water use efficiency, enhanced cold tolerance,] increased yield, [enhanced nitrogen use efficiency, enhanced seed protein,] enhanced seed oil, or modified oil composition.

13. The transgenic plant cell of claim 7 further comprising at least one DNA molecule expressing a protein that provides an enhanced trait as compared to control plant cells; and wherein the enhanced trait is [enhanced water use efficiency, enhanced cold tolerance,] increased yield, [enhanced nitrogen use efficiency, enhanced seed protein,] enhanced seed oil, or modified oil composition.

14. A method for manufacturing non-natural, transgenic plants that can be used to produce a crop of transgenic plant with an enhanced trait resulting from expression of a stably-integrated, recombinant DNA molecule comprising a promoter that is functional in a plant and that is operably linked to a polynucleotide that[, when expressed in a plant that]
encodes a protein:
   i) having the amino acid sequence of SEQ ID NO:5; or
   ii) having an amino acid sequence having at least 90% identity to SEQ ID NO:5, wherein the sequence exhibits diacylglycerol acyltransferase activity said method comprising:
   (a) obtaining a population of plants transformed with said recombinant DNA molecule;
   (b) screening the population of plants for said enhanced trait and said recombinant DNA molecule, wherein individual plants in said population exhibit said trait at a level less than, essentially the same as, or greater than the level that said trait is exhibited in control plants which do not contain said recombinant DNA molecule, wherein said enhanced trait is selected from the group of enhanced traits consisting of enhanced water use efficiency, enhanced cold tolerance, increased yield, enhanced nitrogen use efficiency, enhanced seed protein, enhanced seed oil, and modified oil composition;
   (c) selecting from said population one or more plants that exhibit said trait at a level greater than the level that said trait is exhibited in control plants, and (d) collecting seed from the selected plant or plants from step c [b].

15. The method of claim 14 wherein said method for manufacturing said transgenic seed further comprises:
(a) verifying that said recombinant DNA is stably integrated in said selected plants, and
(b) analyzing tissue of said selected plant to determine the expression of a protein having the function of a protein having the amino acid sequence of SEQ ID NO:5.

16. The method of claim 15 wherein said seed is corn, soybean, cotton, canola, alfalfa, wheat, rice, sugarcane, or sugar beet seed.

17. A recombinant nucleic acid molecule comprising a nucleic acid sequence encoding a polypeptide having diacylglycerol acyltransferase activity, wherein the nucleic acid molecule is
a nucleic acid sequence that encodes a polypeptide comprising a sequence that is at least 95% identical to SEQ ID NO: 5 over its full length.

18. The recombinant, nucleic acid molecule of claim 17, wherein the polypeptide comprises the sequence of SEQ ID NO: 5.

19. The recombinant nucleic acid molecule of claim 17, defined as comprising the nucleic acid sequence of SEQ ID NO: 2.

20. The transgenic plant cell of claim 3 wherein said plant cell is in an algae.

21. Oil derived from the transgenic plant cell of claim 3 that comprises said recombinant DNA molecule.

22. Oil derived from the transgenic plant cell of claim 6 that comprises said recombinant DNA molecule.

23. Oil derived from the transgenic plant cell of claim 7 that comprises said recombinant DNA molecule.

24. Oil derived from the transgenic plant cell of claim 11 that comprises said recombinant DNA molecule.

25. Oil derived from the transgenic plant cell of claim 12 that comprises said recombinant DNA molecule.

26. Oil derived from the transgenic plant cell of claim 13 that comprises said recombinant DNA molecule.

27. Oil derived from the transgenic plant cell of claim 20 that comprises said recombinant DNA molecule.

* * * * *

UNITED STATES PATENT AND TRADEMARK OFFICE
CERTIFICATE OF CORRECTION

PATENT NO. : 8,502,026 B2  Page 1 of 1
APPLICATION NO. : 12/860188
DATED : August 6, 2013
INVENTOR(S) : Maureen Daley et al.

It is certified that error appears in the above-identified patent and that said Letters Patent is hereby corrected as shown below:

In the Claims

Claim 1, Column 61, Line 24, please delete "ammo", and insert --amino--

Claim 2, Column 61, Line 32, please delete "intron, '", and insert --intron, 3'--

Claim 3, Column 61, Line 34, please delete "that functional", and insert --that is functional--

Claim 3, Column 61, Line 35, please delete "to as", and insert --to a--

Signed and Sealed this
Nineteenth Day of November, 2013

Teresa Stanek Rea
*Deputy Director of the United States Patent and Trademark Office*

SEQUENCE LISTING

<160> NUMBER OF SEQ ID NOS: 9

<210> SEQ ID NO 1
<211> LENGTH: 2133
<212> TYPE: DNA
<213> ORGANISM: Glycine max

<400> SEQUENCE: 1

| | | | | | |
|---|---|---|---|---|---|
| ggctcgagtc | cgagcagttt | tagggaaata | cgcaccaggg | tcaacgtccc | cttcatgttc | 60 |
| ttctggccat | gaccaagaga | atagaagctc | tttggatttt | tacactggaa | ttttttggact | 120 |
| tgataagtca | aggataatgg | atacagtaaa | ccaagctatg | gaggagctca | tcaagatggc | 180 |
| taccgtgggg | gaaccattat | ggcttcgtag | cttcgagact | ggtcgcgaaa | ttcttaacta | 240 |
| tgatgaatat | gttagggagt | ttgcagttga | aaattcaagc | agtggaaagc | caaggagatc | 300 |
| cattgaagcc | tcaagagaca | ctgcagttgt | ttttgtggat | ctccctcggc | ttgtccaaag | 360 |
| ttttctagat | gtgaatcagt | ggaaggaaat | gtttccgtgt | ttaatatcta | aggcggccac | 420 |
| tgttgatgta | atatgcaatg | gagagggtcc | tggcaggaat | ggtgcagtgc | aactgatgtt | 480 |
| tgctgagctg | caaatgctca | ctcctatggt | gcccacaaga | gaagtatatt | ttgtccgttt | 540 |
| ctgcaagcag | ttgagtgctg | aacagtgggc | aatcgttgat | gtatccatag | acaaagtaga | 600 |
| agacaacatt | gacgcgtccc | tcgtgaaatg | cagaaaacgc | ccttccggtt | gcattattga | 660 |
| ggacaagtcc | aatggccatt | gcaaagtaat | atgggtggag | cacttggaat | gccagaagag | 720 |
| tgcagtccat | tcaatgtatc | gcaccattgt | gaacagtggc | ctagcttttg | gggccaggca | 780 |
| ttggattgcg | actctacaac | ttcaatgtga | acgtctagtt | ttcttcatgg | caacaaatgt | 840 |
| tcccatgaag | gattcaaccg | tgttgccac | gttggccggg | agaaaaagca | ttttgaagtt | 900 |
| ggcacaaaga | atgacatgga | gtttctgcca | tgcaattggc | gcgtcaagct | tccacacatg | 960 |
| gactaagttt | acaagtaaaa | ctggagaaga | cataaggata | agttctagaa | agaacttgaa | 1020 |
| cgatcctggt | gaacctcttg | ggttgatatt | gtgcgctgtt | tgttctgtat | ggttgcctgt | 1080 |
| ctcacctaat | gttctgtttg | atttcctgag | ggatgaaacg | cgacgaactg | aagtaccact | 1140 |
| ctcttgtctc | ctttccttct | caatcctttt | gtcaattttg | gttaataatt | tgaatggtta | 1200 |
| aatgtcctga | tacgtatcac | attatcttag | tgggacatca | tgtcaagtgg | tgggacagtg | 1260 |
| cagtccattg | caaatttagc | caaaggacaa | gaccgaggaa | atgccgtagc | cattcaagta | 1320 |
| agttacttcg | gttcaaattt | caataccta | aaatgaaaat | gcaaagtgca | ttgaggtaaa | 1380 |
| aaagacatgg | ttctaagtga | aatatggtat | tcttctgatt | tggcagacaa | ttaaatcgaa | 1440 |
| agaaaacagt | gtgtggatac | tgcaagatag | ctacacaaac | ccttatgagt | caatggtggt | 1500 |
| atatgcttct | gtggacatta | ctggcactca | gtctgtgatg | acaggatgtg | attcgagcaa | 1560 |
| tcttgccata | ctgccctcag | gattctctat | tattcctgat | ggtcttgagt | caaggccatt | 1620 |
| ggtgattagt | tcaaggcagg | aagaaaaaaa | taccgaggga | ggatctttgt | ttacaatggc | 1680 |
| attccagatt | cttaccaatg | cttctcccgc | tgccaagtta | acaatggagt | ctgtggactc | 1740 |
| ggtcaacact | cttgtatctt | gtacattgag | aaatatccga | acgagtctac | aatgtgaaga | 1800 |
| tggctagtca | aaatcagata | atcacttgat | agagagtcat | agactttaat | tagctgtgat | 1860 |
| aatcttaggc | tctctattcc | cttttttgga | tggtattcgg | tttggcaaaa | atagcttgct | 1920 |
| tttgtcccct | ttctccgttt | ctgggttagt | tttactcatt | attccactac | caaggagggt | 1980 |
| tggttgagtt | tgtatatctg | tatctgcagt | tctgtaggta | gaaagataga | caaaaagctt | 2040 |

-continued

```
ttagaaccta gagtattaag tatggcgtgt atagaattat catttgttaa ttccttatgc    2100
agttggtttt ttggtaaaaa aaaaaaaaaa agg                                 2133

<210> SEQ ID NO 2
<211> LENGTH: 1047
<212> TYPE: DNA
<213> ORGANISM: Rhodosporidium toruloides

<400> SEQUENCE: 2
atgggccagc aggcgacgcc cgaggagcta tacacacgct cagagatctc caagatcaaa     60
ttcgcaccct tggcgtcccg cggtcgcgc cggctgcaga ccttctccgt ctttgcctgg    120
acgacggcac tgcccatcct actcggcgtc ttcttcctcc tctgctcgtt cccaccgctc    180
tggccggctg tcattgccta cctcacctgg gtcttttca ttgaccaggc gccgattcac    240
ggtggacggg cgcagtcttg gctgcggaag agtcggatat gggtctggtt tgcaggatac    300
tatcccgtca gcttgatcaa gagcgccgac ttgccgcctg accggaagta cgtctttggc    360
taccacccgc acggcgtcat aggcatgggc gccatcgcca acttcgcgac cgacgcaacc    420
ggcttctcga cactcttccc cggcttgaac cctcacctcc tcaccctcca agcaacttc     480 aagctcccgc tctaccgcga gttgctgctc gctctcggca tatgctccgt ctcgatgaag    540
agctgtcaga acattctgcg gcaaggtcct ggctcggctc tcactatcgt cgtcggtggc    600
gccgccgaga gcttgagtgc gcatcccgga accgccgatc ttacgctcaa gcgacgaaaa    660
ggcttcatca aactcgcgat ccggcaaggc gccgacttg tgcccgtctt ttcgttcggc    720
gagaacgaca tctttggcca gctgcgaaac gagcgaggaa cgcggctgta caagttgcag    780 aagcgttcc aaggcgtgtt tggcttcacc ctccctctct tctacggccg gggactcttc    840
aactacaacg tcggattgat gccgtatcgc catccgatcg tctctgtcgt cggtcgacca    900
atctcggtag agcagaagga ccacccgacc acggcggacc tcgaagaagt tcaggcgcgg    960
tatatcgcag aactcaagcg catctgggaa gaatacaagg acgcctacgc caaaagtcgc   1020
acgcgggagc tcaatattat cgcctga                                       1047

<210> SEQ ID NO 3
<211> LENGTH: 1317
<212> TYPE: DNA
<213> ORGANISM: Artificial sequence
<220> FEATURE:
<223> OTHER INFORMATION: Plant

<400> SEQUENCE: 3
atgaaacgcc cacttacgac aagtccgtca agctctagcc caagctcctc tgtttcttct     60
tctactacta cttcctctcc tattcagtcg gaggctccaa ggcctaaacg agccaaaagg    120
gctaagaaat cttctccttc tggtgataaa tctcataacc cgacaagccc tgcttctacc    180
cgacgcagct ctatctacag aggagtcact agacatagat ggactgggag attcgaggct    240
catctttggg acaaaagctc ttggaattcg attcagaaca agaaaggcaa acaagtttat    300
ctgggagcat atgacagtga agaagcagca gcacatacgt acgatctggc tgctctcaag    360
tactggggac ccgacaccat cttgaattt ccggcagaga cgtacacaaa ggaattggaa    420
gaaatgcaga gagtgacaaa ggaagaatat ttggcttctc tccgccgcca gagcagtggt    480
ttctccagag gcgtctctaa atatcgcggc gtcgctaggc atcaccacaa cggaagatgg    540
gaggctcgga tcgaagagt gtttgggaac aagtacttgt acctcggcac ctataatacg    600
caggaggaag ctgctgcagc atatgacatg gctgcgattg agtatcgagg cgcaaacgcg    660
```

```
gttactaatt tcgacattag taattacatt gaccggttaa agaagaaagg tgttttcccg      720
ttccctgtga accaagctaa ccatcaagag ggtattcttg ttgaagccaa acaagaagtt      780
gaaacgagag aagcgaagga agagcctaga gaagaagtga acaacagta cgtggaagaa      840 ccaccgcaag aagaagaaga aaggaagaa gagaaagcag agcaacaaga agcagagatt      900
gtaggatatt cagttgaaga agcagtgatt acctgctgca tagacagctc aaccataatg      960
gaaatggata ggtgtgggga gtcaaatgag ctcgcttggg acttctgtat gatggattca     1020
gggtttgctc cgttttgac tgattcaaat ctctcgagtg agaatcccat tgagtatcct     1080
gagcttttca atgagatggg ttttgaggat aacattgact tcatgttcga ggaagggaag     1140
caagactgct tgagcttgga gaatcttgat tgttgcgatg gtgttgttgt ggtgggaaga     1200
gagagcccaa cttcattgtc gtcttctccg ttgtcctgct tgtctactga ctctgcttca     1260
tcaacaacaa caacagcaac aacagtaacc tctgttagct ggaactatag cgtctag       1317

<210> SEQ ID NO 4
<211> LENGTH: 354
<212> TYPE: PRT
<213> ORGANISM: Glycine max

<400> SEQUENCE: 4

Met Asp Thr Val Asn Gln Ala Met Glu Glu Leu Ile Lys Met Ala Thr
1               5                   10                  15

Val Gly Glu Pro Leu Trp Leu Arg Ser Phe Glu Thr Gly Arg Glu Ile
                20                  25                  30

Leu Asn Tyr Asp Glu Tyr Val Arg Glu Phe Ala Val Glu Asn Ser Ser
            35                  40                  45

Ser Gly Lys Pro Arg Arg Ser Ile Glu Ala Ser Arg Asp Thr Ala Val
        50                  55                  60

Val Phe Val Asp Leu Pro Arg Leu Val Gln Ser Phe Leu Asp Val Asn
65                  70                  75                  80

Gln Trp Lys Glu Met Phe Pro Cys Leu Ile Ser Lys Ala Ala Thr Val
                85                  90                  95

Asp Val Ile Cys Asn Gly Glu Gly Pro Gly Arg Asn Gly Ala Val Gln
                100                 105                 110

Leu Met Phe Ala Glu Leu Gln Met Leu Thr Pro Met Val Pro Thr Arg
            115                 120                 125

Glu Val Tyr Phe Val Arg Phe Cys Lys Gln Leu Ser Ala Glu Gln Trp
        130                 135                 140

Ala Ile Val Asp Val Ser Ile Asp Lys Val Glu Asp Asn Ile Asp Ala
145                 150                 155                 160

Ser Leu Val Lys Cys Arg Lys Arg Pro Ser Gly Cys Ile Ile Glu Asp
                165                 170                 175

Lys Ser Asn Gly His Cys Lys Val Ile Trp Val Glu His Leu Glu Cys
                180                 185                 190

Gln Lys Ser Ala Val His Ser Met Tyr Arg Thr Ile Val Asn Ser Gly
            195                 200                 205

Leu Ala Phe Gly Ala Arg His Trp Ile Ala Thr Leu Gln Leu Gln Cys
        210                 215                 220

Glu Arg Leu Val Phe Phe Met Ala Thr Asn Val Pro Met Lys Asp Ser
225                 230                 235                 240

Thr Gly Val Ala Thr Leu Ala Gly Arg Lys Ser Ile Leu Lys Leu Ala
                245                 250                 255

Gln Arg Met Thr Trp Ser Phe Cys His Ala Ile Gly Ala Ser Ser Phe
                260                 265                 270
```

-continued

His Thr Trp Thr Lys Phe Thr Ser Lys Thr Gly Glu Asp Ile Arg Ile
             275                 280                 285

Ser Ser Arg Lys Asn Leu Asn Asp Pro Gly Glu Pro Leu Gly Leu Ile
        290                 295                 300

Leu Cys Ala Val Cys Ser Val Trp Leu Pro Ser Pro Asn Val Leu
305                 310                 315                 320

Phe Asp Phe Leu Arg Asp Glu Thr Arg Arg Thr Glu Val Pro Leu Ser
                325                 330                 335

Cys Leu Leu Ser Phe Ser Ile Leu Ser Ile Leu Val Asn Asn Leu
                340                 345                 350

Asn Gly

<210> SEQ ID NO 5
<211> LENGTH: 348
<212> TYPE: PRT
<213> ORGANISM: Rhodosporidium toruloides

<400> SEQUENCE: 5

Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

```
Tyr Arg His Pro Ile Val Ser Val Val Gly Arg Pro Ile Ser Val Glu
                290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                    325                 330                 335

Ala Lys Ser Arg Thr Arg Glu Leu Asn Ile Ile Ala
                340                 345

<210> SEQ ID NO 6
<211> LENGTH: 438
<212> TYPE: PRT
<213> ORGANISM: Artificial Sequence
<220> FEATURE:
<223> OTHER INFORMATION: Plant

<400> SEQUENCE: 6

Met Lys Arg Pro Leu Thr Thr Ser Pro Ser Ser Ser Pro Ser Ser
1               5                   10                  15

Ser Val Ser Ser Thr Thr Ser Ser Pro Ile Gln Ser Glu Ala
                20                  25                  30

Pro Arg Pro Lys Arg Ala Lys Ala Lys Lys Ser Ser Pro Ser Gly
            35                  40                  45

Asp Lys Ser His Asn Pro Thr Ser Pro Ala Ser Thr Arg Arg Ser Ser
50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
                    85                  90                  95

Lys Gln Val Tyr Leu Gly Ala Tyr Asp Ser Glu Ala Ala Ala His
                100                 105                 110

Thr Tyr Asp Leu Ala Ala Leu Lys Tyr Trp Gly Pro Asp Thr Ile Leu
                115                 120                 125

Asn Phe Pro Ala Glu Thr Tyr Thr Lys Glu Leu Glu Glu Met Gln Arg
            130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                    165                 170                 175

Asn Gly Arg Trp Glu Ala Arg Ile Gly Arg Val Phe Gly Asn Lys Tyr
                180                 185                 190

Leu Tyr Leu Gly Thr Tyr Asn Thr Gln Glu Glu Ala Ala Ala Ala Tyr
                195                 200                 205

Asp Met Ala Ala Ile Glu Tyr Arg Gly Ala Asn Ala Val Thr Asn Phe
            210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                    245                 250                 255

Lys Gln Glu Val Glu Thr Arg Glu Ala Lys Glu Glu Pro Arg Glu Glu
                260                 265                 270

Val Lys Gln Gln Tyr Val Glu Glu Pro Pro Gln Glu Glu Glu Lys
            275                 280                 285

Glu Glu Glu Lys Ala Glu Gln Gln Ala Glu Ile Val Gly Tyr Ser
290                 295                 300

Val Glu Glu Ala Val Ile Thr Cys Cys Ile Asp Ser Ser Thr Ile Met
```

```
            305                 310                 315                 320
Glu Met Asp Arg Cys Gly Glu Ser Asn Glu Leu Ala Trp Asp Phe Cys
                325                 330                 335

Met Met Asp Ser Gly Phe Ala Pro Phe Leu Thr Asp Ser Asn Leu Ser
                340                 345                 350

Ser Glu Asn Pro Ile Glu Tyr Pro Glu Leu Phe Asn Glu Met Gly Phe
        355                 360                 365

Glu Asp Asn Ile Asp Phe Met Phe Glu Glu Gly Lys Gln Asp Cys Leu
        370                 375                 380

Ser Leu Glu Asn Leu Asp Cys Cys Asp Gly Val Val Val Gly Arg
385                 390                 395                 400

Glu Ser Pro Thr Ser Leu Ser Ser Pro Leu Ser Cys Leu Ser Thr
                405                 410                 415

Asp Ser Ala Ser Ser Thr Thr Thr Thr Ala Thr Thr Val Thr Ser Val
                420                 425                 430

Ser Trp Asn Tyr Ser Val
        435

<210> SEQ ID NO 7
<211> LENGTH: 11722
<212> TYPE: DNA
<213> ORGANISM: Artificial Sequence
<220> FEATURE:
<223> OTHER INFORMATION: Synthetic Construct

<400> SEQUENCE: 7
cgcgcctgcc tgcaggtact cgaggtcatt catatgcttg agaagagagt cgggatagtc      60
caaaataaaa caaaggtaag attacctggt caaaagtgaa acatcagtt aaaaggtggt      120 ataaagtaaa atatcggtaa taaaaggtgg cccaaagtga atttactct tttctactat      180 tataaaaatt gaggatgttt ttgtcggtac tttgatacgt catttttgta tgaattggtt      240
tttaagttta ttcgcttttg gaaatgcata tctgtatttg agtcgggttt taagttcgtt      300
tgcttttgta aatacagagg gatttgtata agaaatatct ttagaaaaac ccatatgcta      360
atttgacata atttttgaga aaaatatata ttcaggcgaa ttctcacaat gaacaataat      420
aagattaaaa tagctttccc ccgttgcagc gcatgggtat tttttctagt aaaaataaaa      480
gataaactta gactcaaaac atttacaaaa acaaccccta agttcctaa agcccaaagt      540 gctatccacg atccatagca agcccagccc aacccaaccc aacccaaccc accccagtcc      600
agccaactgg acaatagtct ccacaccccc ccactatcac cgtgagttgt ccgcacgcac      660
cgcacgtctc gcagccaaaa aaaaaagaa agaaaaaaaa gaaaaagaaa aaacagcagg      720
tgggtccggg tcgtgggggc cggaaacgcg aggaggatcg cgagccagcg acgaggagct      780
taggcctcat cgttgaagat gcctctgccg acagtggtcc caaagatgga cccccaccca      840
cgaggagcat cgtggaaaaa gaagacgttc caaccacgtc ttcaaagcaa gtggattgat      900
gtgatatctc cactgacgta agggatgacg cacaatccca ctatccttcg aggcctcatc      960
gttgaagatg cctctgccga cagtggtccc aaagatggac ccccacccac gaggagcatc     1020
gtggaaaaag aagacgttcc aaccacgtct tcaaagcaag tggattgatg tgatatctcc     1080
actgacgtaa gggatgacgc acaatccac tatccttcga agctccctcc ctccgcttcc     1140
aaagaaacgc ccccatcgc cactatatac ataccccccc ctctcctccc atcccccaa     1200 cccttctaga accatcttcc acacactcaa gccacactat tggagaacac acagggacaa     1260
cacaccataa gatccaaggg aggcctccgc cgccgccggt aaccaccccg cccctctcct     1320
```

```
ctttctttct ccgtttttttt ttccgtctcg gtctcgatct ttggccttgg tagtttgggt    1380
gggcgagagg cggcttcgtg cgcgcccaga tcggtgcgcg ggaggggcgg gatctcgcgg    1440
ctggggctct cgccggcgtg gatccggccc ggatctcgcg gggaatgggg ctctcggatg    1500
tagatctgcg atccgccgtt gttggggggag atgatggggg gtttaaaatt tccgccgtgc    1560
taaacaagat caggaagagg ggaaaagggc actatggttt atatttttat atatttctgc    1620
tgcttcgtca ggcttagatg tgctagatct ttcttcttc tttttgtggg tagaatttga    1680
atccctcagc attgttcatc ggtagttttt cttttcatga tttgtgacaa atgcagcctc    1740
gtgcggagct ttttttgtagg tagaagcgga ccggtcgcgc tcagcagtc gctgtcgtta    1800 acccagcggt actcgctgag gcgatcgcgg gcccggtacc ctgcaatgtg accctagact    1860
tgtccatctt ctggattggc caacttaatt aatgtatgaa ataaaaggat gcacacatag    1920
tgacatgcta atcactataa tgtgggcatc aaagttgtgt gttatgtgta attactaatt    1980
atctgaataa gagaaagaga tcatccatat ttcttatcct aaatgaatgt cacgtgtctt    2040
tataattctt tgatgaacca gatgcatttt attaaccaat tccatataca tataaatatt    2100
aatcatatat aattaatatc aattgggtta gcaaaacaaa tctagtctag gtgtgttttg    2160
ctaattattg ggggatagtg caaaaagaaa tctacgttct caataattca gatagaaaac    2220
ttaataaagt gagataattt acatagattg cttttatcct ttgatatatg tgaaaccatg    2280
catgatataa ggaaaataga tagagaaata atttttttaca tcgttgaata tgtaaacaat    2340
ttaattcaag aagctaggaa tataaatatt gaggagttta tgattattat tattatttg    2400 atgttcaatg aagtttttt taatttcata tgaagtatac aaaaattctt catagatttt    2460
tgtttctatg ccgtagttat ctttaatata tttgtggttg aagaaattta ttgctagaaa    2520
cgaatggatt gtcaattttt ttttaaagca aatatatatg aaattatact gtatattatt    2580
ttagtcatga ttaaaatgtg gccttaattg aatcatcttt ctcattcatt tttcaaaag    2640 catatcagga tgattgatat ttatctatt taaaaattaa tttaagggtt caaattaaat    2700
ttaacttaaa agtgtcctaa ccgtagttaa aggtttactt taaaaaaata ctatgaaaaa    2760
tctaatcttc tatgaatcga cctgcaggat ttaaatccat cgttctgggg cctaacgggc    2820
caagcttact cgaggtcatt catatgcttg agaagagagt cgggatagtc caaaataaaa    2880
caaaggtaag attacctggt caaaagtgaa aacatcagtt aaaaggtggt ataaagtaaa    2940
atatcggtaa taaaaggtgg cccaaagtga aatttactct tttctactat tataaaaatt    3000
gaggatgttt ttgtcggtac tttgatacgt catttttgta tgaattggtt tttaagttta    3060
ttcgcttttg gaaatgcata tctgtatttg agtcgggttt taagttcgtt tgcttttgta    3120
aatacagagg gatttgtata agaaatatct ttagaaaaac ccatatgcta atttgacata    3180
atttttgaga aaaatatata ttcaggcgaa ttctcacaat gaacaataat aagattaaaa    3240
tagctttccc ccgttgcagc gcatgggtat ttttttctagt aaaaataaaa gataaactta    3300
gactcaaaac atttacaaaa acaaccccta aagttcctaa agcccaaagt gctatccacg    3360
atccatagca agcccagccc aacccaaccc aacccaaccc accccagtcc agccaactgg    3420
acaatagtct ccacaccccc ccactatcac cgtgagttgt ccgcacgcac cgcacgtctc    3480
gcagccaaaa aaaaaagaa agaaaaaaaa gaaaagaaaa aacagcagg tgggtccggg    3540 tcgtggggc cggaaacgcg aggaggatcg cgagccagcg acgaggccgg ccctccctcc    3600
gcttccaaag aaacgccccc catcgccact atatacatac ccccccctct cctcccatcc    3660
ccccaaccct accaccacca ccaccaccac ctccacctcc tcccccctcg ctgccggacg    3720
```

```
acgagctcct ccccccctccc cctccgccgc cgccgcgccg gtaaccaccc cgcccctctc    3780
ctctttcttt ctccgttttt ttttccgtct cggtctcgat ctttggcctt ggtagtttgg    3840
gtgggcgaga ggcggcttcg tgcgcgccca gatcggtgcg cgggaggggc gggatctcgc    3900
ggctggggct ctccgcggcg tggatccggc ccgatctcg cggggaatgg ggctctcgga     3960
tgtagatctg cgatccgccg ttgttggggg agatgatggg gggtttaaaa tttccgccgt    4020
gctaaacaag atcaggaaga ggggaaaagg gcactatggt ttatatttt atatatttct     4080 gctgcttcgt caggcttaga tgtgctagat cttctttct tctttttgtg ggtagaattt     4140
gaatccctca gcattgttca tcggtagttt ttcttttcat gatttgtgac aaatgcagcc    4200
tcgtgcggag cttttttgta ggtagaagtg atcaaccatg gcgcaagtta gcagaatctg    4260
caatggtgtg cagaacccat ctcttatctc caatctctcg aaatccagtc aacgcaaatc    4320
tcccttatcg gtttctctga agacgcagca gcatccacga gcttatccga tttcgtcgtc    4380
gtggggattg aagaagagtg ggatgacgtt aattggctct gagcttcgtc ctcttaaggt    4440
catgtcttct gtttccacgg cgtgcatgct tcacggtgca agcagccggc ccgcaaccgc    4500
ccgcaaatcc tctggccttt ccggaaccgt ccgcattccc ggcgacaagt cgatctccca    4560
ccggtccttc atgttcggcg gtctcgcgag cggtgaaacg cgcatcaccg gccttctgga    4620
aggcgaggac gtcatcaata cgggcaaggc catgcaggcg atgggcgccc gcatccgtaa    4680
ggaaggcgac acctggatca tcgatggcgt cggcaatggc ggcctcctgg cgcctgaggc    4740
gccgctcgat ttcggcaatg ccgccacggg ctgccgcctg acgatgggcc tcgtcggggt    4800
ctacgatttc gacagcacct tcatcggcga cgcctcgctc acaaagcgcc cgatgggccg    4860
cgtgttgaac ccgctgcgcg aaatgggcgt gcaggtgaaa tcggaagacg gtgaccgtct    4920
tcccgttacc ttgcgcgggc cgaagacgcc gacgccgatc acctaccgcg tgccgatggc    4980
ctccgcacag gtgaagtccg ccgtgctgct cgccggcctc aacacgcccg gcatcacgac    5040
ggtcatcgag ccgatcatga cgcgcgatca tacgaaaaag atgctgcagg gctttggcgc    5100
caaccttacc gtcgagacgg atgcggacgg cgtgcgcacc atccgcctgg aaggccgcgg    5160
caagctcacc ggccaagtca tcgacgtgcc gggcgacccg tcctcgacgg ccttcccgct    5220
ggttgcggcc ctgcttgttc cgggctccga cgtcaccatc ctcaacgtgc tgatgaaccc    5280 caccccgcacc ggcctcatcc tgacgctgca ggaaatgggc gccgacatcg aagtcatcaa    5340
cccgcgcctt gccggcggcg aagacgtggc ggacctgcgc gttcgctcct ccacgctgaa    5400
gggcgtcacg gtgccggaag accgcgcgcc ttcgatgatc gacgaatatc cgattctcgc    5460
tgtcgccgcc gccttcgcgg aagggcgac cgtgatgaac ggtctggaag aactccgcgt    5520
caaggaaagc gaccgcctct cggccgtcgc caatggcctc aagctcaatg gcgtggattg    5580
cgatgagggc gagacgtcgc tcgtcgtgcg tggccgccct gacggcaagg ggctcggcaa    5640
cgcctcgggc gccgccgtcg ccacccatct cgatcaccgc atcgccatga gcttcctcgt    5700
catgggcctc gtgtcggaaa accctgtcac ggtggacgat gccacgatga tcgccacgag    5760
cttcccggag ttcatggacc tgatggccgg gctgggcgcg aagatcgaac tctccgatac    5820
gaaggctgcc tgatgagctc gaattcccga tcgttcaaac atttggcaat aaagtttctt    5880
aagattgaat cctgttgccg gtcttgcgat gattatcata taatttctgt tgaattacgt    5940
taagcatgta ataattaaca tgtaatgcat gacgttattt atgagatggg ttttatgat    6000 tagagtcccg caattataca tttaatacgc gatagaaaac aaaatatagc gcgcaaacta    6060
ggataaatta tcgcgcgcgg tgtcatctat gttactagat cggggatggg ggatccacta    6120
```

-continued

```
gtgatatccg tcgactggta cctacgcgta gctagcccgt gaagtttctc atctaagccc    6180
ccatttggac gtgaatgtag acacgtcgaa ataaagattt ccgaattaga ataatttgtt    6240
tattgctttc gcctataaat acgacggatc gtaatttgtc gttttatcaa aatgtacttt    6300
catttttataa taacgctgcg gacatctaca ttttttgaatt gaaaaaaaat tggtaattac    6360
tctttctttt tctccatatt gaccatcata ctcattgctg atccatgtag atttcccgga    6420
catgaagcca tttacaattg aatatatcct gccgccgctg ccgctttgca cccggtggag    6480
cttgcatgtt ggtttctacg cagaactgag ccggttaggc agataatttc cattgagaac    6540
tgagccatgt gcaccttccc cccaacacgg tgagcgacgg ggcaacggag tgatccacat    6600
gggactttc ctagcttggc tgccattttt ggggtgaggc cgttcgcggc cgagggcgc    6660
agcccctggg gggatgggag gcccgcgtta gcgggccggg agggttcgag aaggggggc    6720
accccccttc ggcgtgcgcg gtcacgcgca cagggcgcag ccctggttaa aaacaaggtt    6780
tataaatatt ggtttaaaag caggttaaaa gacaggttag cggtggccga aaaacgggcg    6840
gaaacccttg caaatgctgg atttttctgcc tgtggacagc ccctcaaatg tcaataggtg    6900
cgcccctcat ctgtcagcac tctgcccctc aagtgtcaag gatcgcgccc ctcatctgtc    6960
agtagtcgcg cccctcaagt gtcaataccg cagggcactt atccccaggc ttgtccacat    7020
catctgtggg aaactcgcgt aaaatcaggc gttttcgccg atttgcgagg ctggccagct    7080
ccacgtcgcc ggccgaaatc gagcctgccc ctcatctgtc aacgccgcgc cgggtgagtc    7140
ggcccctcaa gtgtcaacgt ccgcccctca tctgtcagtg agggccaagt tttccgcgag    7200
gtatccacaa cgccggcggc cggccgcggt gtctcgcaca cggcttcgac ggcgtttctg    7260
gcgcgtttgc agggccatag acggccgcca gcccagcggc gagggcaacc agcccggtga    7320
gcgtcggaaa gggtcgatcg accgatgccc ttgagagcct tcaacccagt cagctccttc    7380
cggtgggcgc ggggcatgac tatcgtcgcc gcacttatga ctgtcttctt tatcatgcaa    7440
ctcgtaggac aaggtgccgg cagcgctctgg gtcatttttcg gcgaggaccg ctttcgctgg    7500
agcgcgacga tgatcggcct gtcgcttgcg gtattcggaa tcttgcacgc cctcgctcaa    7560
gccttcgtca ctggtcccgc caccaaacgt ttcggcgaga agcaggccat tatcgccggc    7620
atggcggccg acgcgctggg ctacgtcttg ctggcgttcg cgacgcgagg ctggatggcc    7680
ttccccatta tgattcttct cgcttccggc ggcatcggga tgcccgcgtt gcaggccatg    7740
ctgtccaggc aggtagatga cgaccatcag ggacagcttc aaggatcgct cgcggctctt    7800
accagcctaa cttcgatcat tggaccgctg atcgtcacgg cgatttatgc cgcctcggcg    7860
agcacatgga acgggttggc atggattgta ggcgccgccc tataccttgt ctgcctcccc    7920
gcgttgcgtc gcggtgcatg gagccgggcc acctcgacct gaatggaagc cggcggcacc    7980
tcgctaacgg attcaccact ccaagaattg gagccaatca attcttgcgg agaactgtga    8040
atgcgcaaac caaccccttgg cagaacatat ccatcgcgtc cgccatctcc agcagccgca    8100
cgcggcgcat ctcgggcagc gttgggtcct ggccacgggt gcgcatgatc gtgctcctgt    8160
cgttgaggac ccggctaggc tggcgggggtt gccttactgg ttagcagaat gaatcaccga    8220
tacgcgagcg aacgtgaagc gactgctgct gcaaaacgtc tgcgacctga gcaacaacat    8280
gaatggtctt cggtttccgt gtttcgtaaa gtctggaaac gcggaagtca gcgccctgca    8340
ccattatgtt ccggatctgc atcgcaggat gctgctggct accctgtgga acacctacat    8400
ctgtattaac gaagcgctgg cattgaccct gagtgatttt tctctggtcc cgccgcatcc    8460
ataccgccag ttgtttaccc tcacaacgtt ccagtaaccg ggcatgttca tcatcagtaa    8520
```

```
cccgtatcgt gagcatcctc tctcgtttca tcggtatcat tacccccatg aacagaaatc   8580
cccctttacac ggaggcatca gtgaccaaac aggaaaaaac cgcccttaac atggcccgct   8640
ttatcagaag ccagacatta acgcttctgg agaaactcaa cgagctggac gcggatgaac   8700
aggcagacat ctgtgaatcg cttcacgacc acgctgatga gctttaccgc agctgcctcg   8760
cgcgtttcgg tgatgacggt gaaaacctct gacacatgca gctcccggag acggtcacag   8820
cttgtctgta agcggatgcc gggagcagac aagcccgtca gggcgcgtca gcgggtgttg   8880
gcgggtgtcg gggcgcagcc atgacccagt cacgtagcga tagcggagtg tatactggct   8940
taactatgcg gcatcagagc agattgtact gagagtgcac catatgcggt gtgaaatacc   9000
gcacagatgc gtaaggagaa ataccgcat caggcgctct ccgcttcct cgctcactga    9060
ctcgctgcgc tcggtcgttc ggctgcggcg agcggtatca gctcactcaa aggcggtaat   9120
acggttatcc acagaatcag gggataacgc aggaaagaac atgtgagcaa aaggccagca   9180
aaaggccagg aaccgtaaaa aggccgcgtt gctggcgttt ttccataggc tccgcccccc   9240
tgacgagcat cacaaaaatc gacgctcaag tcagaggtgg cgaaacccga caggactata   9300
aagataccag gcgtttcccc ctggaagctc cctcgtgcgc tctcctgttc cgaccctgcc   9360
gcttaccgga tacctgtccg cctttctccc ttcgggaagc gtggcgcttt ctcatagctc   9420
acgctgtagg tatctcagtt cggtgtaggt cgttcgctcc aagctgggct gtgtgcacga   9480
accccccgtt cagcccgacc gctgcgcctt atccggtaac tatcgtcttg agtccaaccc   9540
ggtaagacac gacttatcgc cactggcagc agccactggt aacaggatta gcagagcgag   9600
gtatgtaggc ggtgctacag agttcttgaa gtggtggcct aactacggct acactagaag   9660
gacagtattt ggtatctgcg ctctgctgaa gccagttacc ttcggaaaaa gagttggtag   9720
ctcttgatcc ggcaaacaaa ccaccgctgg tagcggtggt ttttttgttt gcaagcagca   9780
gattacgcgc agaaaaaaag gatctcaaga agatcctttg atcttttcta cggggtctga   9840
cgctcagtgg aacgaaaact cacgttaagg gattttggtc atgagattat caaaaaggat   9900
cttcacctag atccttttaa attaaaaatg aagttttaaa tcaatctaaa gtatatatga   9960
gtaaacttgg tctgacagtt accaatgctt aatcagtgag gcacctatct cagcgatctg  10020
tctatttcgt tcatccatag ttgcctgact ccccgtcgtg tagataacta cgatacggga  10080
gggcttacca tctggcccca gtgctgcaat gataccgcga gacccacgct caccggctcc  10140
agatttatca gcaataaacc agccagccgg aagggccgag cgcagaagtg gtcctgcaac  10200
tttatccgcc tccatccagt ctattaattg ttgccgggaa gctagagtaa gtagttcgcc  10260
agttaatagt ttgcgcaacg ttgttgccat tgctgcaggt cgggagcaca ggatgacgcc  10320
taacaattca ttcaagccga caccgcttcg cggcgcggct taattcagga gttaaacatc  10380
atgagggaag cggtgatcgc cgaagtatcg actcaactat cagaggtagt tggcgtcatc  10440
gagcgccatc tcgaaccgac gttgctggcc gtacatttgt acggctccgc agtggatggc  10500
ggcctgaagc cacacagtga tattgatttg ctggttacgg tgaccgtaag gcttgatgaa  10560
acaacgcggc gagctttgat caacgacctt ttggaaactt cggcttcccc tggagagagc  10620
gagattctcc gcgctgtaga agtcaccatt gttgtgcacg acgacatcat tccgtggcgt  10680
tatccagcta agcgcgaact gcaatttgga gaatggcagc gcaatgacat tcttgcaggt  10740
atcttcgagc cagccacgat cgacattgat ctggctatct tgctgacaaa agcaagagaa  10800
catagcgttg ccttggtagg tccagcggcg gaggaactct ttgatccggt tcctgaacag  10860
gatctatttg aggcgctaaa tgaaacctta acgctatgga actcgccgcc cgactgggct  10920
```

-continued

```
ggcgatgagc gaaatgtagt gcttacgttg tcccgcattt ggtacagcgc agtaaccggc    10980
aaaatcgcgc cgaaggatgt cgctgccgac tgggcaatgg agcgcctgcc ggcccagtat    11040
cagcccgtca tacttgaagc taggcaggct tatcttggac aagaagatcg cttggcctcg    11100
cgcgcagatc agttggaaga atttgttcac tacgtgaaag gcgagatcac caaggtagtc    11160
ggcaaataat gtctaacaat tcgttcaagc cgacgccgct tcgcggcgcg cttaactca     11220
agcgttagat gctgcaggca tcgtggtgtc acgctcgtcg tttggtatgg cttcattcag    11280
ctccggttcc caacgatcaa ggcgagttac atgatccccc atgttgtgca aaaaagcggt    11340
tagctccttc ggtcctccga tcgaggattt tcggcgctg cgctacgtcc gcgaccgcgt     11400
tgagggatca agccacagca gcccactcga ccttctagcc gacccagacg agccaaggga    11460
tcttttggga atgctgctcc gtcgtcaggc tttccgacgt ttgggtggtt gaacagaagt    11520
cattatcgca cggaatgcca agcactcccg aggggaaccc tgtggttggc atgcacatac    11580
aaatggacga acgataaac cttttcacgc ccttttaaat atccgattat tctaataaac     11640
gctcttttct cttaggttta cccgccaata tatcctgtca aacactgata gtttaaactg    11700
aaggcgggaa acgacaatct gg                                             11722
```

<210> SEQ ID NO 8
<211> LENGTH: 9769
<212> TYPE: DNA
<213> ORGANISM: Artificial Sequence
<220> FEATURE:
<223> OTHER INFORMATION: Synthetic Construct

<400> SEQUENCE: 8

```
ggtccgatgt gagactttc aacaaagggt aatatccgga aacctcctcg gattccattg       60
cccagctatc tgtcactta ttgtgaagat agtggaaaag gaaggtggct cctacaaatg       120
ccatcattgc gataaaggaa aggccatcgt tgaagatgcc tctgccgaca gtggtcccaa      180
agatggaccc ccacccacga ggagcatcgt ggaaaaagaa gacgttccaa ccacgtcttc      240
aaagcaagtg gattgatgtg atggtccgat tgagactttt caacaaaggg taatatccgg      300
aaacctcctc ggattccatt gcccagctat ctgtcacttt attgtgaaga tagtggaaaa      360
ggaaggtggc tcctacaaat gccatcattg cgataaagga aaggccatcg ttgaagatgc      420
ctctgccgac agtggtccca agatggaccc ccacccacg aggagcatcg tggaaaaaga      480
agacgttcca accacgtctt caaagcaagt ggattgatgt gatatctcca ctgacgtaag     540
ggatgacgca caatcccact atccttcgca agacccttcc tctatataag gaagttcatt      600
tcatttggag aggaccaggt ggtaccggcg cgcctcagca gtcgctgtcg ttaacccagc      660
ggtactcgct gaggcgatcg cgggccctga tcacctgtcg tacagtattt ctacatttga      720
tgtgtgattt gtgaagaaca tcaaacaaaa caagcactgg ctttaatatg atgataagta      780
ttatggtaat taattaattg gcaaaaacaa caatgaagct aaaatttat ttattgagcc       840
ttgcggttaa tttcttgtga tgatcttttt ttttattttc taattatata gtttccctt       900
tgctttgaaa tgctaaaggt ttgagagagt tatgctcttt ttttcttcct ctttcttttt     960
taactttatc atacaaattt tgaataaaaa tgtgagtaca ttgagctcat ttaaataagc     1020
ttgatgggga tcagattgtc gtttcccgcc ttcagtttaa actatcagtg tttgacagga    1080
tatattggcg ggtaaaccta agagaaaaga gcgtttatta gaataatcgg atatttaaaa    1140
gggcgtgaaa aggtttatcc gttcgtccat ttgtatgtgc atgccaacca cagggttccc    1200
ctcgggagtg cttggcattc cgtgcgataa tgacttctgt tcaaccaccc aaacgtcgga    1260
```

```
aagcctgacg acggagcagc attccaaaaa gatcccttgg ctcgtctggg tcggctagaa    1320
ggtcgagtgg gctgctgtgg cttgatccct aacgcggtc gcggacgtag cgcagcgccg     1380
aaaaatcctc gatcggagga ccgaaggagc taaccgcttt tttgcacaac atgggggatc    1440
atgtaactcg ccttgatcgt tgggaaccgg agctgaatga agccatacca aacgacgagc    1500
gtgacaccac gatgcctgca gcatctaacg cttgagttaa gccgcgccgc gaagcggcgt    1560
cggcttgaac gaattgttag acattatttg ccgactacct tggtgatctc gcctttcacg    1620
tagtgaacaa attcttccaa ctgatctgcg cgcgaggcca agcgatcttc ttgtccaaga    1680
taagcctgcc tagcttcaag tatgacgggc tgatactggg ccggcaggcg ctccattgcc    1740
cagtcggcag cgacatcctt cggcgcgatt ttgccggtta ctgcgctgta ccaaatgcgg    1800
gacaacgtaa gcactacatt tcgctcatcg ccagcccagt cgggcggcga gttccatagc    1860
gttaaggttt catttagcgc ctcaaataga tcctgttcag gaaccggatc aaagagttcc    1920
tccgccgctg gacctaccaa ggcaacgcta tgttctcttg cttttgtcag caagatagcc    1980
agatcaatgt cgatcgtggc tggctcgaag atacctgcaa gaatgtcatt gcgctgccat    2040
tctccaaatt gcagttcgcg cttagctgga taacgccacg gaatgatgtc gtcgtgcaca    2100
acaatggtga cttctacagc gcggagaatc tcgctctctc caggggaagc cgaagtttcc    2160
aaaaggtcgt tgatcaaagc tcgccgcgtt gtttcatcaa gccttacggt caccgtaacc    2220
agcaaatcaa tatcactgtg tggcttcagg ccgccatcca ctgcggagcc gtacaaatgt    2280
acggccagca acgtcggttc gagatggcgc tcgatgacgc caactacctc tgatagttga    2340
gtcgatactt cggcgatcac cgcttccctc atgatgttta actcctgaat taagccgcgc    2400
cgcgaagcgg tgtcggcttg aatgaattgt taggcgtcat cctgtgctcc cgacctgcag    2460
caatggcaac aacgttgcgc aaactattaa ctggcgaact acttactcta gcttcccggc    2520
aacaattaat agactggatg gaggcggata aagttgcagg accacttctg cgctcggccc    2580
ttccggctgg ctggtttatt gctgataaat ctggagccgg tgagcgtggg tctcgcggta    2640
tcattgcagc actggggcca gatggtaagc cctcccgtat cgtagttatc tacacgacgg    2700
ggagtcaggc aactatggat gaacgaaata gacagatcgc tgagataggt gcctcactga    2760
ttaagcattg gtaactgtca gaccaagttt actcatatat actttagatt gatttaaaac    2820 ttcatttta atttaaaagg atctaggtga agatccttt tgataatctc atgaccaaaa      2880
tcccttaacg tgagttttcg ttccactgag cgtcagaccc cgtagaaaag atcaaaggat    2940
cttcttgaga tccttttttt ctgcgcgtaa tctgctgctt gcaaacaaaa aaaccaccgc    3000
taccagcggt ggtttgtttg ccggatcaag agctaccaac tctttttccg aaggtaactg    3060
gcttcagcag agcgcagata ccaaatactg tccttctagt gtagccgtag ttaggccacc    3120
acttcaagaa ctctgtagca ccgcctacat acctcgctct gctaatcctg ttaccagtgg    3180
ctgctgccaa tggcgataag tcgtgtctta ccgggttgga ctcaagacga tagttaccgg    3240
ataaggcgca gcggtcgggc tgaacggggg gttcgtgcac acagcccagc ttggagcgaa    3300
cgacctacac cgaactgaga tacctacagc gtgagctatg agaaagcgcc acgcttcccg    3360
aagggagaaa ggcggacagg tatccggtaa gcggcagggt cggaacagga gagcgcacga    3420
gggagcttcc agggggaaac gcctggtatc tttatagtcc tgtcgggttt cgccacctct    3480
gacttgagcg tcgatttttg tgatgctcgt caggggggcg gagcctatgg aaaaacgcca    3540
gcaacgcggc ctttttacgg ttcctggcct tttgctggcc ttttgctcac atgttctttc    3600
ctgcgttatc ccctgattct gtggataacc gtattaccgc ctttgagtga gctgataccg    3660
```

```
ctcgccgcag ccgaacgacc gagcgcagcg agtcagtgag cgaggaagcg gaagagcgcc    3720
tgatgcggta ttttctcctt acgcatctgt gcggtatttc acaccgcata tggtgcactc    3780
tcagtacaat ctgctctgat gccgcatagt taagccagta tacactccgc tatcgctacg    3840
tgactgggtc atggctgcgc cccgacaccc gccaacaccc gctgacgcgc cctgacgggc    3900
ttgtctgctc ccggcatccg cttacagaca agctgtgacc gtctccggga gctgcatgtg    3960
tcagaggttt tcaccgtcat caccgaaacg cgcgaggcag ctgcggtaaa gctcatcagc    4020
gtggtcgtga agcgattcac agatgtctgc ctgttcatcc gcgtccagct cgttgagttt    4080
ctccagaagc gttaatgtct ggcttctgat aaagcgggcc atgttaaggg cggttttttc    4140
ctgtttggtc actgatgcct ccgtgtaagg gggatttctg ttcatggggg taatgatacc    4200
gatgaaacga gagaggatgc tcacgatacg ggttactgat gatgaacatg cccggttact    4260
ggaacgttgt gagggtaaac aactggcggt atggatgcgg cgggaccaga gaaaaatcac    4320
tcagggtcaa tgccagcgct tcgttaatac agatgtaggt gttccacagg gtagccagca    4380
gcatcctgcg atgcagatcc ggaacataat ggtgcagggc gctgacttcc gcgtttccag    4440
actttacgaa acacggaaac gaagaccat tcatgttgtt gctcaggtcg cagacgtttt    4500
gcagcagcag tcgcttcacg ttcgctcgcg tatcggtgat tcattctgct aaccagtaag    4560
gcaaccccgc cagcctagcc gggtcctcaa cgacaggagc acgatcatgc gcacccgtgg    4620
ccaggaccca acgctgcccg agatgcgccg cgtgcggctg ctggagatgg cggacgcgat    4680
ggatatgttc tgccaagggt tggtttgcgc attcacagtt ctccgcaaga attgattggc    4740
tccaattctt ggagtggtga atccgttagc gaggtgccgc cggcttccat tcaggtcgag    4800
gtggcccggc tccatgcacc gcgacgcaac gcggggaggc agacaaggta tagggcggcg    4860
cctacaatcc atgccaaccc gttccatgtg ctcgccgagg cggcataaat cgccgtgacg    4920
atcagcggtc caatgatcga agttaggctg gtaagagccg cgagcgatcc ttgaagctgt    4980
ccctgatggt cgtcatctac ctgcctggac agcatggcct gcaacgcggg catcccgatg    5040
ccgccggaag cgagaagaat cataatgggg aaggccatcc agcctcgcgt cgcgaacgcc    5100
agcaagacgt agcccagcgc gtcggccgcc atgccggcga taatggcctg cttctcgccg    5160
aaacgtttgg tggcgggacc agtgacgaag gcttgagcga gggcgtgcaa gattccgaat    5220
accgcaagcg acaggccgat catcgtcgcg ctccagcgaa agcggtcctc gccgaaaatg    5280
acccagagcg ctgccggcac ctgtcctacg agttgcatga taaagaagac agtcataagt    5340
gcggcgacga tagtcatgcc ccgcgcccac cggaaggagc tgactgggtt gaaggctctc    5400
aagggcatcg gtcgatcgac cctttccgac gctcaccggg ctggttgccc tcgccgctgg    5460
gctggcggcc gtctatggcc ctgcaaacgc gccagaaacg ccgtcgaagc cgtgtgcgag    5520
acaccgcggc cggccgccgg cgttgtggat acctcgcgga aaacttggcc ctcactgaca    5580
gatgaggggc ggacgttgac acttgagggg ccgactcacc cggcgcggcg ttgacagatg    5640 agggcaggc tcgatttcgg ccggcgacgt ggagctggcc agcctcgcaa atcggcgaaa    5700
acgcctgatt ttacgcgagt ttcccacaga tgatgtggac aagcctgggg ataagtgccc    5760
tgcggtattg acacttgagg ggcgcgacta ctgacagatg aggggcgcga tccttgacac    5820
ttgaggggca gagtgctgac agatgagggg cgcacctatt gacatttgag gggctgtcca    5880
caggcagaaa atccagcatt tgcaagggtt ccgcccgtt tttcggccac cgctaacctg    5940
tcttttaacc tgcttttaaa ccaatattta taaaccttgt ttttaaccag ggctgcgccc    6000
tgtgcgcgtg accgcgcacg ccgaagggg gtgccccccc ttctcgaacc ctcccggccc    6060
```

```
gctaacgcgg gcctcccatc cccccagggg ctgcgcccct cggccgcgaa cggcctcacc    6120
ccaaaaatgg cagccaagct aggaaaagtc ccatgtggat cactccgttg ccccgtcgct    6180
caccgtgttg gggggaaggt gcacatggct cagttctcaa tggaaattat ctgcctaacc    6240
ggctcagttc tgcgtagaaa ccaacatgca agctccaccg ggtgcaaagc ggcagcggcg    6300
gcaggatata ttcaattgta atggcttca tgtccgggaa atctacatgg atcagcaatg    6360
agtatgatgg tcaatatgga gaaaagaaa gagtaattac caatttttt tcaattcaaa    6420 aatgtagatg tccgcagcgt tattataaaa tgaaagtaca ttttgataaa acgacaaatt    6480
acgatccgtc gtatttatag gcgaaagcaa taaacaaatt attctaattc ggaaatcttt    6540
atttcgacgt gtctacattc acgtccaaat gggggcttag atgagaaact tcacgatcga    6600
tgcggccacc actcgagaag cttactagtc aacaattggc caatctttgt tctaaattgc    6660
taataaacga ccatttccgt caattctcct tggttgcaac agtctacccg tcaaatgttt    6720
actaatttat aagtgtgaag tttgaattat gaaagacgaa atcgtattaa aaattcacaa    6780
gaataaacaa ctccatagat tttcaaaaaa acagtcacga gaaaaaaacc acagtccgtt    6840
tgtctgctct tctagttttt attattttc tattaatagt ttttttgttat ttcgagaata    6900 aaatttgaac gatgtccgaa ccacaaaagc cgagccgata aatcctaagc cgagcctaac    6960
tttagccgta accatcagtc acggctcccg ggctaattca tttgaaccga atcataatca    7020
acggtttaga tcaaactcaa aacaatctaa cggcaacata gacgcgtcgg tgagctaaaa    7080
agagtgtgaa agccaggtca ccatagcatt gtctctccca gatttttat ttgggaaata    7140 atagaagaaa tagaaaaaaa taaagagtg agaaaaatcg tagagctata tattcgcaca    7200
tgtactcgtt tcgctttcct tagtgttagc tgctgccgct gttgtttctc ctccatttct    7260
ctatctttct ctctcgctgc ttctcgaatc ttctgtatca tcttcttctt cttcaaggtg    7320
agtctctaga tccgttcgct tgattttgct gctcgttagt cgttattgtt gattctctat    7380
gccgatttcg ctagatctgt ttagcatgcg ttgtggtttt atgagaaaat ctttgttttg    7440
ggggttgctt gttatgtgat tcgatccgtg cttgttggat cgatctgagt taattcttaa    7500
ggtttatgtg ttagatctat ggagtttgag gattcttctc gcttctgtcg atctctcgct    7560 gttattttg ttttttcag tgaagtgaag ttgtttagtt cgaaatgact tcgtgtatgc    7620
tcgattgatc tggttttaat cttcgatctg ttaggtgttg atgttacaa gtgaattcta    7680 gtgttttctc gttgagatct gtgaagtttg aacctagttt tctcaataat caacatatga    7740
agcgatgttt gagtttcaat aaacgctgct aatcttcgaa actaagttgt gatctgattc    7800
gtgtttactt catgagctta tccaattcat ttcggtttca ttttacttt ttttagtga    7860 accatggcgc aagttagcag aatctgcaat ggtgtgcaga acccatctct tatctccaat    7920
ctctcgaaat ccagtcaacg caaatctccc ttatcggttt ctctgaagac gcagcagcat    7980
ccacgagctt atccgatttc gtcgtcgtgg ggattgaaga agagtgggat gacgttaatt    8040
ggctctgagc ttcgtcctct taaggtcatg tcttctgttt ccacggcgtg catgcttcat    8100
ggagcttcat ctaggccagc tactgccagg aagtctagcg ggctcagtgg caccgtgcgc    8160
atccctggcg ataaaagtat ttcacacagg agcttcatgt tcggaggact tgctagtgga    8220
gagacgagaa tcactggttt gcttgagggc gaagatgtta tcaacaccgg taaggcgatg    8280
caagcaatgg gtgccagaat ccgaaagag ggcgatacgt ggatcatcga cggtgttggt    8340
aacggaggat tgctcgctcc cgaagcgcca cttgactttg gaacgcagc tacggggtgc    8400 cgtcttacta tgggactggt aggcgtgtat gactttgact ctaccttcat cggtgacgcg    8460
```

```
agcctcacta agagaccaat gggacgagtg ctgaatcccc tgagggagat gggtgtccag      8520
gtgaaatctg aggatggtga tcgtcttccg gttactctgc gaggcccccaa gaccccccacg    8580 ccaatcacgt acagggttcc gatggcgtca gcacaggtca agtcagcggt actcctggcg     8640
ggcctcaaca cacctggaat cacaaccgtg attgaaccca tcatgactag agaccacacg     8700
gagaagatgt tgcagggttt cggcgctaat ctaacggtcg aaaccgacgc cgacggcgtg     8760
aggacaatcc gcttggaggg cagaggtaaa ctgactggcc aagtcatcga tgtgcctgga     8820
gatccctcgt ccacagcgtt tccctcgta gctgcgttgc tcgtccctgg atctgatgtg     8880
acgatcctga atgtcctcat gaatccaact agaaccggcc tcatcctcac attgcaggag    8940
atgggtgctg acatcgaggt tatcaatcct aggttggcag gtggagagga tgtggccgat     9000
ctgcgcgtgc gttctagtac actcaaaggc gtgaccgtcc ctgaggatcg cgctccatcc     9060
atgatcgacg agtaccccat tctcgccgtt gctgctgcgt ttgccgaggg cgcaactgta     9120
atgaacggcc ttgaggagtt gagggttaag gagagtgaca ggctgtccgc ggtggcgaat     9180
ggcctgaagc taaacggcgt ggactgcgac gaaggtgaaa cgtcccttgt agtccgtggt     9240
cgcccagacg ggaaggggtt ggggaatgct tcgggagctg ctgtggcgac gcaccttgat     9300
catagaatcg ccatgtcatt tctggtgatg ggacttgtct ccgagaatcc ggtgaccgtt     9360
gacgatgcta ccatgatcgc cacctccttt cctgagttca tggacctcat ggcaggcttg     9420
ggggccaaga tcgagctgtc tgatactaag gccgcttgaa ttcccgatcg ttcaaacatt     9480
tggcaataaa gtttcttaag attgaatcct gttgccggtc ttgcgatgat tatcatataa     9540
tttctgttga attacgttaa gcatgtaata attaacatgt aatgcatgac gttatttatg     9600
agatgggttt ttatgattag agtcccgcaa ttatacattt aatacgcgat agaaaacaaa     9660
atatagcgcg caaactagga taaattatcg cgcgcggtgt catctatgtt actagatcgg     9720
ggatcccacg tgcggaccgc ctgcaggccg cgttatcaag ctaactgca                 9769
```

<210> SEQ ID NO 9
<211> LENGTH: 8504
<212> TYPE: DNA
<213> ORGANISM: Artificial Sequence
<220> FEATURE:
<223> OTHER INFORMATION: Synthetic Construct

<400> SEQUENCE: 9

```
aggattttc ggcgctgcgc tacgtccgcg accgcgttga gggatcaagc cacagcagcc      60
cactcgacct tctagccgac ccagacgagc caagggatct ttttggaatg ctgctccgtc    120
gtcaggcttt ccgacgttg gtggttgaa cagaagtcat tatcgcacgg aatgccaagc     180
actcccgagg ggaaccctgt ggttggcatg cacatacaaa tggacgaacg gataaacctt    240
ttcacgccct tttaaatatc cgattattct aataaacgct cttttctctt aggtttaccc    300
gccaatatat cctgtcaaac actgatagtt taaactgaag cgggaaacg acaatctgat     360 ccccatcaag cttggccagc ttctgcaggt ccgattgaga cttttcaaca aagggtaata    420
tccggaaacc tcctcggatt ccattgccca gctatctgtc actttattgt gaagatagtg    480
gaaaaggaag gtggctccta caaatgccat cattgcgata aaggaaaggc catcgttgaa    540
gatgcctctg ccgacagtgg tcccaaagat ggaccccccac ccacgaggag catcgtggaa   600
aaagaagacg ttccaaccac gtcttcaaag caagtggatt gatgtgatgg tccgattgag    660
acttttcaac aaagggtaat atccggaaac ctcctcggat tccattgccc agctatctgt    720
cactttattg tgaagatagt ggaaaaggaa ggtggctcct acaaatgcca tcattgcgat    780
```

| | |
|---|---|
| aaaggaaagg ccatcgttga agatgcctct gccgacagtg gtcccaaaga tggaccccca | 840 |
| cccacgagga gcatcgtgga aaaagaagac gttccaacca cgtcttcaaa gcaagtggat | 900 |
| tgatgtgata tctccactga cgtaagggat gacgcacaat cccactatcc ttcgcaagac | 960 |
| ccttcctcta tataaggaag ttcatttcat ttggagagga cacagaaaaa tttgctacat | 1020 |
| tgtttcacaa acttcaaata ttattcattt atttgtcagc tttcaaactc tttgtttctt | 1080 |
| gtttgttgat tagatctggt accctcagca gtcgctgtgc gatcgccagc ggtactcgct | 1140 |
| gaggtcgacg tagttagtta attcagcttt cgttcgtatc atcggtttcg acaacgttcg | 1200 |
| tcaagttcaa tgcatcagtt tcattgcgca cacaccagaa tcctactgag tttgagtatt | 1260 |
| atggcattgg gaaaactgtt tttcttgtac catttgttgt gcttgtaatt tactgtgttt | 1320 |
| tttattcggt tttcgctatc gaactgtgaa atggaaatgg atggagaaga gttaatgaat | 1380 |
| gatatggtcc ttttgttcat tctcaaatta atattatttg ttttttctct tatttgttgt | 1440 |
| gtgttgaatt tgaaattata agagatatgc aaacattttg ttttgagtaa aaatgtgtca | 1500 |
| aatcgtggcc tctaatgacc gaagttaata tgaggagtaa aacacttgta gttgtaccat | 1560 |
| tatgcttatt cactaggcaa caaatatatt ttcagaccta gaaaagctgc aaatgttact | 1620 |
| gaatacaagt atgtcctctt gtgttttaga catttatgaa cttttcctta tgtaattttc | 1680 |
| cagaatcctt gtcagattct aatcattgct ttataattat agttatactc atggatttgt | 1740 |
| agttgagtat gaaaatattt tttaatgcat tttatgactt gccaattgat tgacaacgcg | 1800 |
| gccgccactc gagtggaagc tagctttccg atcctacctg tcacttcatc aaaaggacag | 1860 |
| tagaaaagga aggtggcacc tacaaatgcc atcattgcga taaggaaag gctatcattc | 1920 |
| aagatgcctc tgccgacagt ggtcccaaag atggaccccc acccacgagg agcatcgtgg | 1980 |
| aaaaagaaga cgttccaacc acgtcttcaa agcaagtgga ttgatgtgat acttccactg | 2040 |
| acgtaaggga tgacgcacaa tcccactatc cttcgcaaga cccttcctct atataaggaa | 2100 |
| gttcatttca tttggagagg acacgctgaa atcaccagtc tctctctaca agatcgggga | 2160 |
| tctctagcta gacgatcgtt tcgcatgatt gaacaagatg gattgcacgc aggttctccg | 2220 |
| gccgcttggg tggagaggct attcggctat gactgggcac aacagacaat cggctgctct | 2280 |
| gatgccgccg tgttccggct gtcagcgcag gggcgcccgg ttcttttgt caagaccgac | 2340 |
| ctgtccggtg ccctgaatga actgcaggac gaggcagcgc ggctatcgtg gctggccacg | 2400 |
| acgggcgttc cttgcgcagc tgtgctcgac gttgtcactg aagcgggaag ggactggctg | 2460 |
| ctattgggcg aagtgccggg gcaggatctc ctgtcatctc accttgctcc tgccgagaaa | 2520 |
| gtatccatca tggctgatgc aatgcggcgg ctgcatacgc ttgatccggc tacctgccca | 2580 |
| ttcgaccacc aagcgaaaca tcgcatcgag cgagcacgta ctcggatgga agccggtctt | 2640 |
| gtcgatcagg atgatctgga cgaagagcat caggggctcg cgccagccga actgttcgcc | 2700 |
| aggctcaagg cgcgcatgcc cgacggcgag gatctcgtcg tgacccatgg cgatgcctgc | 2760 |
| ttgccgaata tcatggtgga aaatggccgc ttttctggat tcatcgactg tggccggctg | 2820 |
| ggtgtggcgg accgctatca ggacatagcg ttggctaccc gtgatattgc tgaagagctt | 2880 |
| ggcggcgaat gggctgaccg cttcctcgtg ctttacggta tcgccgctcc cgattcgcag | 2940 |
| cgcatcgcct tctatcgcct tcttgacgag ttcttctgag cgggactctg gggttcgatc | 3000 |
| cccaattccc gatcgttcaa acatttggca ataaagtttc ttaagattga atcctgttgc | 3060 |
| cggtcttgcg atgattatca tataatttct gttgaattac gttaagcatg taataattaa | 3120 |
| catgtaatgc atgacgttat ttatgagatg ggttttatg attagagtcc cgcaattata | 3180 |

```
catttaatac gcgatagaaa acaaaatata gcgcgcaaac taggataaat tatcgcgcgc    3240
ggtgtcatct atgttactag atcggggatc gggccactcg agtggtggcc gcatcgatcg    3300
tgaagtttct catctaagcc cccatttgga cgtgaatgta gacacgtcga aataaagatt    3360
tccgaattag aataatttgt ttattgcttt cgcctataaa tacgacggat cgtaatttgt    3420
cgttttatca aaatgtactt tcattttata ataacgctgc ggacatctac attttttgaat   3480 tgaaaaaaaa ttggtaatta ctctttcttt ttctccatat tgaccatcat actcattgct    3540
gatccatgta gatttcccgg acatgaagcc atttacaatt gaatatatcc tgccgccgct    3600
gccgctttgc acccggtgga gcttgcatgt tggtttctac gcagaactga gccggttagg    3660
cagataattt ccattgagaa ctgagccatg tgcaccttcc ccccaacacg gtgagcgacg    3720
gggcaacgga gtgatccaca tgggactttt cctagcttgg ctgccatttt tggggtgagg    3780
ccgttcgcgg ccgaggggcg cagcccctgg ggggatggga ggcccgcgtt agcgggccgg    3840
gagggttcga aaggggggg cacccccctt cggcgtgcgc ggtcacgcgc acagggcgca    3900
gccctggtta aaaacaaggt ttataaatat tggtttaaaa gcaggttaaa agacaggtta    3960
gcggtggccg aaaaacgggc ggaaacccctt gcaaatgctg gattttctgc ctgtggacag   4020
cccctcaaat gtcaataggt gcgcccctca tctgtcagca ctctgcccct caagtgtcaa    4080
ggatcgcgcc cctcatctgt cagtagtcgc gcccctcaag tgtcaatacc gcagggcact    4140
tatccccagg cttgtccaca tcatctgtgg gaaactcgcg taaaatcagg cgttttcgcc    4200
gatttgcgag gctggccagc tccacgtcgc ggccgaaat cgagcctgcc cctcatctgt    4260
caacgccgcg ccgggtgagt cggcccctca agtgtcaacg tccgcccctc atctgtcagt    4320
gagggccaag ttttccgcga ggtatccaca acgccggcgg ccggccgcgg tgtctcgcac    4380
acggcttcga cggcgtttct ggcgcgtttg cagggccata gacggccgcc agcccagcgg    4440
cgagggcaac cagcccggtg agcgtcggaa agggtcgatc gaccgatgcc cttgagagcc    4500
ttcaacccag tcagctcctt ccggtgggcg cggggcatga ctatcgtcgc cgcacttatg    4560
actgtcttct ttatcatgca actcgtagga caggtgccgg cagcgctctg gtcattttc    4620 ggcgaggacc gctttcgctg gagcgcgacg atgatcggcc tgtcgcttgc ggtattcgga    4680
atcttgcacg ccctcgctca agccttcgtc actggtcccg ccaccaaacg tttcggcgag    4740
aagcaggcca ttatcgccgg catggcggcc gacgcgctgg gctacgtctt gctggcgttc    4800
gcgacgcgag gctggatggc cttccccatt atgattcttc tcgcttccgg cggcatcggg    4860
atgcccgcgt tgcaggccat gctgtccagg caggtagatg acgaccatca gggacagctt    4920
caaggatcgc tcgcggctct taccagccta acttcgatca ttggaccgct gatcgtcacg    4980
gcgatttatg ccgcctcggc gagcacatgg aacgggttgg catggattgt aggcgccgcc    5040
ctataccttg tctgcctccc gcgttgcgt cgcggtgcat ggagccgggc cacctcgacc    5100
tgaatggaag ccgcggcac ctcgctaacg gattcaccac tccaagaatt ggagccaatc    5160
aattcttgcg gagaactgtg aatgcgcaaa ccaacccttg gcagaacata tccatcgcgt    5220
ccgccatctc cagcagccgc acgcggcgca tctcggcag cgttgggtcc tggccacggg    5280
tgcgcatgat cgtgctcctg tcgttgagga cccggctagg ctggcggggt tgccttactg    5340
gttagcagaa tgaatcaccg atacgcgagc gaacgtgaag cgactgctgc tgcaaaacgt    5400
ctgcgacctg agcaacaaca tgaatggtct tcggtttccg tgtttcgtaa agtctggaaa    5460
cgcggaagtc agcgccctgc accattatgt tccggatctg catcgcagga tgctgctggc    5520
taccctgtgg aacacctaca tctgtattaa cgaagcgctg gcattgaccc tgagtgattt    5580
```

```
ttctctggtc ccgccgcatc cataccgcca gttgtttacc ctcacaacgt tccagtaacc    5640
gggcatgttc atcatcagta acccgtatcg tgagcatcct ctctcgtttc atcggtatca    5700
ttacccccat gaacagaaat ccccttaca cggaggcatc agtgaccaaa caggaaaaaa     5760
ccgcccttaa catggcccgc tttatcagaa gccagacatt aacgcttctg gagaaactca    5820
acgagctgga cgcggatgaa caggcagaca tctgtgaatc gcttcacgac cacgctgatg    5880
agctttaccg cagctgcctc gcgcgtttcg gtgatgacgg tgaaaacctc tgacacatgc    5940
agctcccgga gacggtcaca gcttgtctgt aagcggatgc cgggagcaga caagcccgtc    6000
agggcgcgtc agcgggtgtt ggcgggtgtc ggggcgcagc catgacccag tcacgtagcg    6060
atagcggagt gtatactggc ttaactatgc ggcatcagag cagattgtac tgagagtgca    6120
ccatatgcgg tgtgaaatac cgcacagatg cgtaaggaga aaataccgca tcaggcgctc    6180
ttccgcttcc tcgctcactg actcgctgcg ctcggtcgtt cggctgcggc gagcggtatc    6240
agctcactca aaggcggtaa tacggttatc cacagaatca ggggataacg caggaaagaa    6300
catgtgagca aaaggccagc aaaaggccag gaaccgtaaa aaggccgcgt tgctggcgtt    6360
tttccatagg ctccgccccc ctgacgagca tcacaaaaat cgacgctcaa gtcagaggtg    6420
gcgaaacccg acaggactat aaagatacca ggcgtttccc cctggaagct ccctcgtgcg    6480
ctctcctgtt ccgaccctgc cgcttaccgg atacctgtcc gcctttctcc cttcgggaag    6540
cgtggcgctt tctcatagct cacgctgtag gtatctcagt tcggtgtagg tcgttcgctc    6600
caagctgggc tgtgtgcacg aaccccccgt tcagcccgac cgctgcgcct tatccggtaa    6660
ctatcgtctt gagtccaacc cggtaagaca cgacttatcg ccactggcag cagccactgg    6720
taacaggatt agcagagcga ggtatgtagg cggtgctaca gagttcttga agtggtggcc    6780
taactacggc tacactagaa ggacagtatt tggtatctgc gctctgctga agccagttac    6840
cttcggaaaa agagttggta gctcttgatc cggcaaacaa accaccgctg gtagcggtgg    6900
tttttttgtt tgcaagcagc agattacgcg cagaaaaaaa ggatctcaag aagatccttt    6960
gatcttttct acggggtctg acgctcagtg gaacgaaaac tcacgttaag ggattttggt    7020
catgagatta tcaaaaagga tcttcaccta gatccttta aattaaaaat gaagttttaa    7080
atcaatctaa agtatatatg agtaaacttg gtctgacagt taccaatgct taatcagtga    7140
ggcacctatc tcagcgatct gtctatttcg ttcatccata gttgcctgac tccccgtcgt    7200
gtagataact acgatacggg agggcttacc atctggcccc agtgctgcaa tgataccgcg    7260
agacccacgc tcaccggctc cagatttatc agcaataaac cagccagccg aagggccga    7320 gcgcagaagt ggtcctgcaa ctttatccgc ctccatccag tctattaatt gttgccggga    7380
agctagagta agtagttcgc cagttaatag tttgcgcaac gttgttgcca ttgctgcagg    7440
tcgggagcac aggatgacgc ctaacaattc attcaagccg acaccgcttc gcggcgcggc    7500
ttaattcagg agttaaacat catgagggaa gcggtgatcg ccgaagtatc gactcaacta    7560
tcagaggtag ttggcgtcat cgagcgccat ctcgaaccga cgttgctggc cgtacatttg    7620
tacggctccg cagtggatgg cggcctgaag ccacacagtg atattgattt gctggttacg    7680
gtgaccgtaa ggcttgatga acaacgcgg cgagctttga tcaacgacct tttggaaact    7740
tcggcttccc ctggagagag cgagattctc cgcgctgtag aagtcaccat tgttgtgcac    7800
gacgacatca ttccgtggcg ttatccagct aagcgcgaac tgcaatttgg agaatggcag    7860
cgcaatgaca ttcttgcagg tatcttgag ccagccacga tcgacattga tctggctatc    7920
ttgctgacaa aagcaagaga acatagcgtt gccttggtag gtccagcggc ggaggaactc    7980
```

```
tttgatccgg ttcctgaaca ggatctattt gaggcgctaa atgaaacctt aacgctatgg    8040
aactcgccgc ccgactgggc tggcgatgag cgaaatgtag tgcttacgtt gtcccgcatt    8100
tggtacagcg cagtaaccgg caaaatcgcg ccgaaggatg tcgctgccga ctgggcaatg    8160
gagcgcctgc cggcccagta tcagcccgtc atacttgaag ctaggcaggc ttatcttgga    8220
caagaagatc gcttggcctc gcgcgcagat cagttggaag aatttgttca ctacgtgaaa    8280
ggcgagatca ccaaggtagt cggcaaataa tgtctaacaa ttcgttcaag ccgacgccgc    8340
ttcgcggcgc ggcttaactc aagcgttaga tgctgcaggc atcgtggtgt cacgctcgtc    8400
gtttggtatg gcttcattca gctccggttc ccaacgatca aggcgagtta catgatcccc    8460
catgttgtgc aaaaaagcgg ttagctcctt cggtcctccg atcg                    8504
```